United States Patent
Dekel et al.

(10) Patent No.: US 10,883,994 B2
(45) Date of Patent: Jan. 5, 2021

(54) IDENTIFICATION OF CANCER STEM CELLS MARKERS AND USE OF SAME FOR DIAGNOSIS AND TREATMENT

(71) Applicant: Tel HaShomer Medical Research Infrastructure and Services Ltd., Ramat-Gan (IL)

(72) Inventors: Benjamin Dekel, Tel-Aviv (IL); Orit Harari-Steinberg, RaAnana (IL)

(73) Assignee: Tel HaShomer Medical Research Infrastructure and Services Ltd., Ramat-Gan (IL)

(*) Notice: Subject to any disclaimer, the term of this patent is extended or adjusted under 35 U.S.C. 154(b) by 0 days.

(21) Appl. No.: 15/320,847

(22) PCT Filed: Jun. 25, 2015

(86) PCT No.: PCT/IL2015/050663
§ 371 (c)(1),
(2) Date: Dec. 21, 2016

(87) PCT Pub. No.: WO2015/198334
PCT Pub. Date: Dec. 30, 2015

(65) Prior Publication Data
US 2017/0199195 A1 Jul. 13, 2017

Related U.S. Application Data

(60) Provisional application No. 62/016,773, filed on Jun. 25, 2014.

(51) Int. Cl.
*G01N 33/574* (2006.01)
*G01N 33/50* (2006.01)
*A61K 31/275* (2006.01)
*C12Q 1/6886* (2018.01)

(52) U.S. Cl.
CPC ..... *G01N 33/57407* (2013.01); *A61K 31/275* (2013.01); *C12Q 1/6886* (2013.01); *G01N 33/5073* (2013.01); *G01N 33/5088* (2013.01); *G01N 33/57484* (2013.01); *C12Q 2600/158* (2013.01); *G01N 2333/90203* (2013.01)

(58) Field of Classification Search
CPC .................................................. G01N 33/57407
See application file for complete search history.

(56) References Cited

U.S. PATENT DOCUMENTS

| 8,435,346 B2 | 5/2013 | Wicha et al. |
| 2011/0111434 A1 | 5/2011 | Huang et al. |
| 2011/0311495 A1 | 12/2011 | Dekel |
| 2013/0260385 A1 | 10/2013 | Dylla et al. |
| 2014/0037644 A1 | 2/2014 | Clarke et al. |

FOREIGN PATENT DOCUMENTS

| CN | 101855339 | 10/2010 |
| CN | 101868534 | 10/2010 |
| WO | WO 2009/120100 | 10/2009 |
| WO | WO 2015/198334 | 12/2015 |

OTHER PUBLICATIONS

Liu et al., PNAS, 2010, vol. 107, No. 42, pp. 18115-18120 (Year: 2010).*
Sivanathan et al., Prostate, 2014, vol. 74, pp. 537-546 (Year: 2014).*
Leibovici, Cancer Research, 1984, vol. 44, pp. 1981-1984 (Year: 1984).*
Moro et al., J. Biomed. Biotech., 2012, Article ID 568567 (Year: 2012).*
Julien et al., Clin. Cancer Res., 2012, vol. 18, No. 19, pp. 5314-5328 (Year: 2012).*
Search Report and Written Opinion dated Jun. 19, 2017 From the Intellectual Property Office of Singapore, IPOS Re. Application No. 11201610630R. (14 Pages).
Galvin et al. "Growth Characteristics of Human Wilms' Tumor in Nude Mice", Pediatric Pathology, 8(6): 599-615, 1988.
Lau et al. "CD44v8-10 Is a Cancer-Specific Marker for Gastric Cancer Stem Cells", Cancer Research, 74(9): 2630-2641, Published Online Mar. 11, 2014. Figs.4C, 4D, p. 2635.
Communication Relating to the Results of the Partial International Search dated Oct. 9, 2015 From the International Searching Authority Re. Application No. PCT/IL2015/050663.
International Preliminary Report on Patentability dated Jan. 5, 2017 From the International Bureau of WIPO Re. Application No. PCT/IL2015/050663.
International Search Report and the Written Opinion dated Dec. 18, 2015 From the International Searching Authority Re. Application No. PCT/IL2015/050663.
Ghani et al. "Identification of Cancer Stem Cell Markers in Human Malignant Mesothelioma Cells", Biochemical and Biophysical Research Communications, XP027597453, 404(2): 735-742, Available Online Dec. 14, 2010.
Ginn et al. "Atypical Teratoid Rhabdoid Tumor: Current Therapy and Future Directions", Frontiers in Oncology, XP055215425, 2(Art.114): 1-13, Sep. 12, 2012.
Hollingshead et al. "Gene Expression Profiling of 49 Human Tumor Xenografts From In Vitro Culture Through Multiple In Vivo Passages—Strategies for Data Mining in Support of Therapeutic Studies", BMC Genomics, 15(393): 1-16, 2014.

(Continued)

*Primary Examiner* — Raymond J Henley, III

(57) ABSTRACT

A method of identifying cancer stem cell markers in a human primary tumor is disclosed. The method comprises:
(a) in vivo passaging the primary tumor; and
(b) comparing a level of at least one antigen in a first population of passaged tumor cells of the primary tumor with a second population of tumor cells of the primary tumor,
wherein an increase in the amount of the antigen in the first population of tumor cells as compared to the amount of the antigen in the second population of tumor cells is indicative of a cancer stem cell marker in the human primary tumor.

Figure 1C:
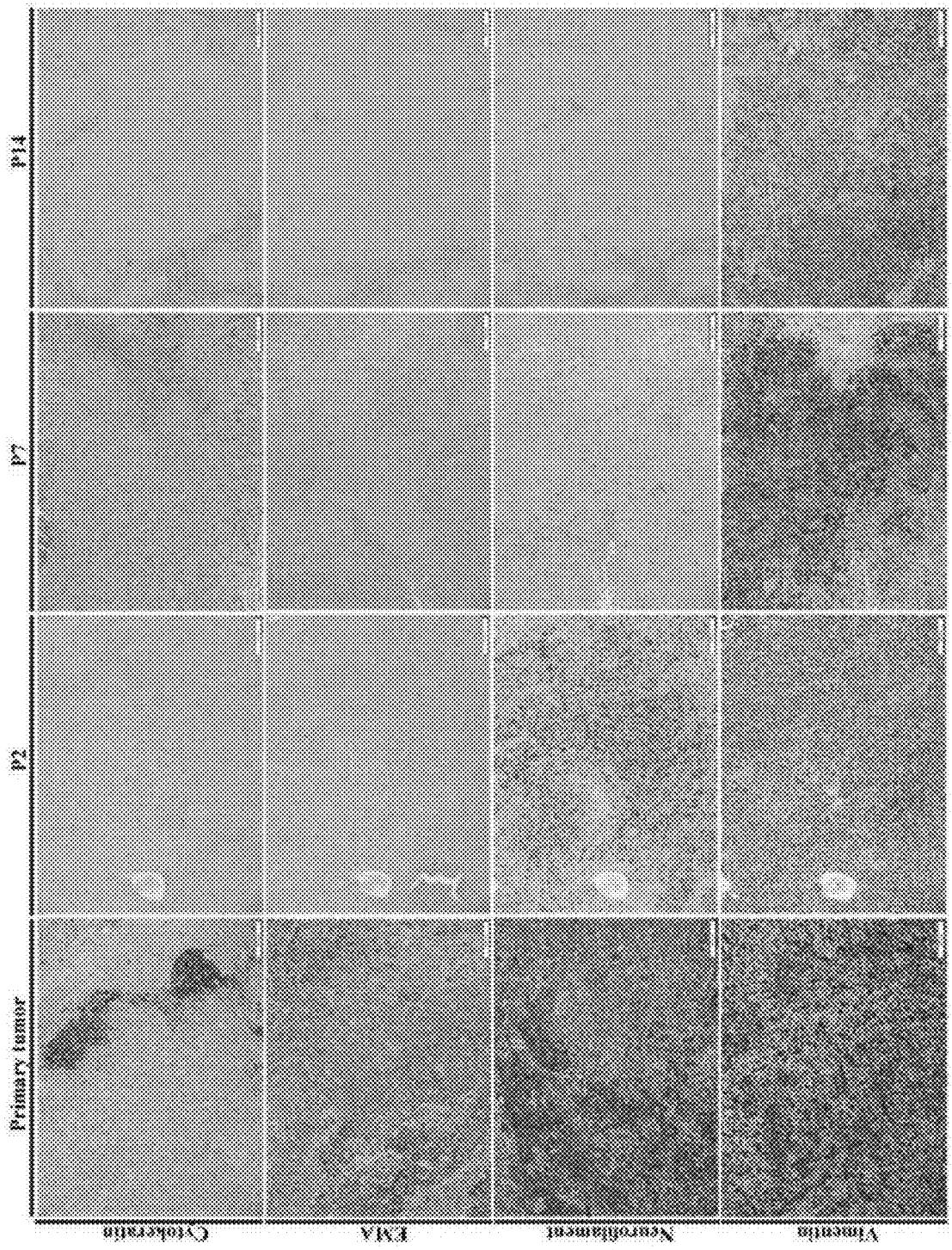

9 Claims, 20 Drawing Sheets
(18 of 20 Drawing Sheet(s) Filed in Color)

(56) References Cited

OTHER PUBLICATIONS

Metildi et al. "Serial In Vivo Orthotopic Passage of Human Pancreatic Cancer Cells Selects for Increased Stem Cell-Like Behavior", Proceedings of the 105th Annual Meeting of the American Association for Cancer Research 2014, San Diego, CA, USA, Apr. 5-9, 2014, AACR, Cancer Research, XP055215943, 74(19 Suppl): Abstract # 4960, Oct. 1, 2014. Abstract.
Metsuyanim et al. "Accumulation of Malignant Renal Stem Cells Is Associated With Epigenetic Changes in Normal Renal Progenitor Genes", Stem Cells, XP002658726, 26(7): 1808-1817, Jul. 2008. Abstract, p. 1809, 1-h col., Para 2, Para "Establishment and Maintenance of WT Xenografts", "PgG Gene Expression in Renal Tumorigenesis", Fig.3.
Pode-Shakked et al. "Developmental Tumourigenesis: NCAM as a Putative Marker for the Malignant Renal Stem/Progenitor Cell Population", Journal of Cellular and Molecular Medicine, XP002581529, 13(8B): 1792-1808, Aug. 2009. Abstract, p. 1793, 1-h col., Para 3.
Pode-Shakked et al. "The Isolation and Characterization of Renal Cancer Initiating Cells From Hurnan Wilms' Tumour Xenografts Unveils New Therapeutic Targets", EMBO Molecular Medicine, XP055215424, 5(1): 18-37, Published Online Dec. 13, 2012. Abstract, p. 23, r-h col., Para 2, Para "Aldehyde Dehydrogenase 1 (ALDH1) Expression Defines the CIC/CSC Within the NCAM+ Cell Population", In Vivo Xenograft Experiments, "In Vivo Targeting of NCAM+ WT Cells With a Humanized Anti-NCAM Antibody-Drug Conjugate (Lorvotuxamab-Mertansine) Eliminates WT Xenografts", Fig.1, Table 1.
Shenoy et al. "ALDH as a Marker for Enriching Tumorigenic Human Colonic Stem Cells", Methods in Molecular Biology, 916: 373-385, 2012.
Shuknm et al. "Targeted Therapy Aimed at Cancer Stem Cells: Wilms' Tumor as an Example", Pediatric Nephrology, XP055215875, 29(5): 815-823, Published Online Jun. 13, 2013. Abstract, Para "Cancer Stem Cells in Wilms' Tumors", "Targeted Therapy—Targeting CSCs in WT", P.3, 1-h col., Para 1-2, Fig.5.
Communication Under Rule 164(2)(a) EPC dated Dec. 21, 2017 From the European Patent Office Re. Application No. 15739030.3. (6 Pages).
Notification of Office Action and Search Report dated Nov. 10, 2017 From the State Intellectual Property Office of the People's Republic of China Re. Application No. 201580037960.8 and Its Summary in English. (11 Pages).
Translation of Notification of Office Action and Search Report dated Nov. 10, 2017 From the State Intellectual Property Office of the People's Republic of China Re. Application No. 201580037960.8. (9 Pages).
Written Opinion dated May 21, 2018 From the Intellectual Property Office of Singapore, IPOS Re. Application No. 11201610630R. (8 Pages).
Notification of Office Action dated Jul. 6, 2018 From the State Intellectual Property Office of the People's Republic of China Re. Application No. 201580037960.8 and Its Summary in English. (5 Pages).
Translation dated Jul. 19, 2018 of Notification of Office Action dated Jul. 6, 2018 From the State Intellectual Property Office of the People's Republic of China Re. Application No. 201580037960.8. (3 Pages).
Communication Pursuant to Article 94(3) EPC dated May 7, 2018 From the European Patent Office Re. Application No. 15739030.3. (6 Pages).
Communication Pursuant to Article 94(3) EPC dated Dec. 21, 2018 From the European Patent Office Re. Application No. 15739030.3. (4 Pages).
Office Action dated Oct. 28, 2018 From the Israel Patent Office Re. Application No. 249741 and Its Translation Into English. (7 Pages).

\* cited by examiner

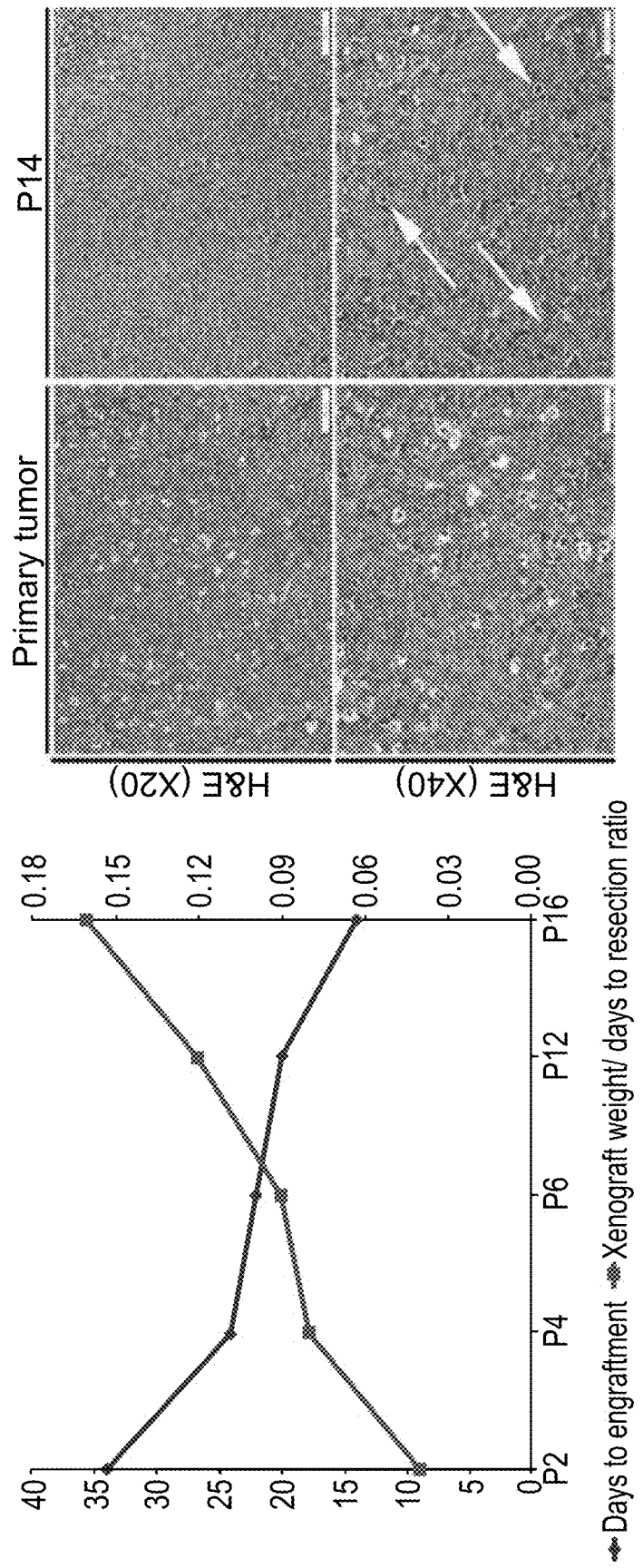

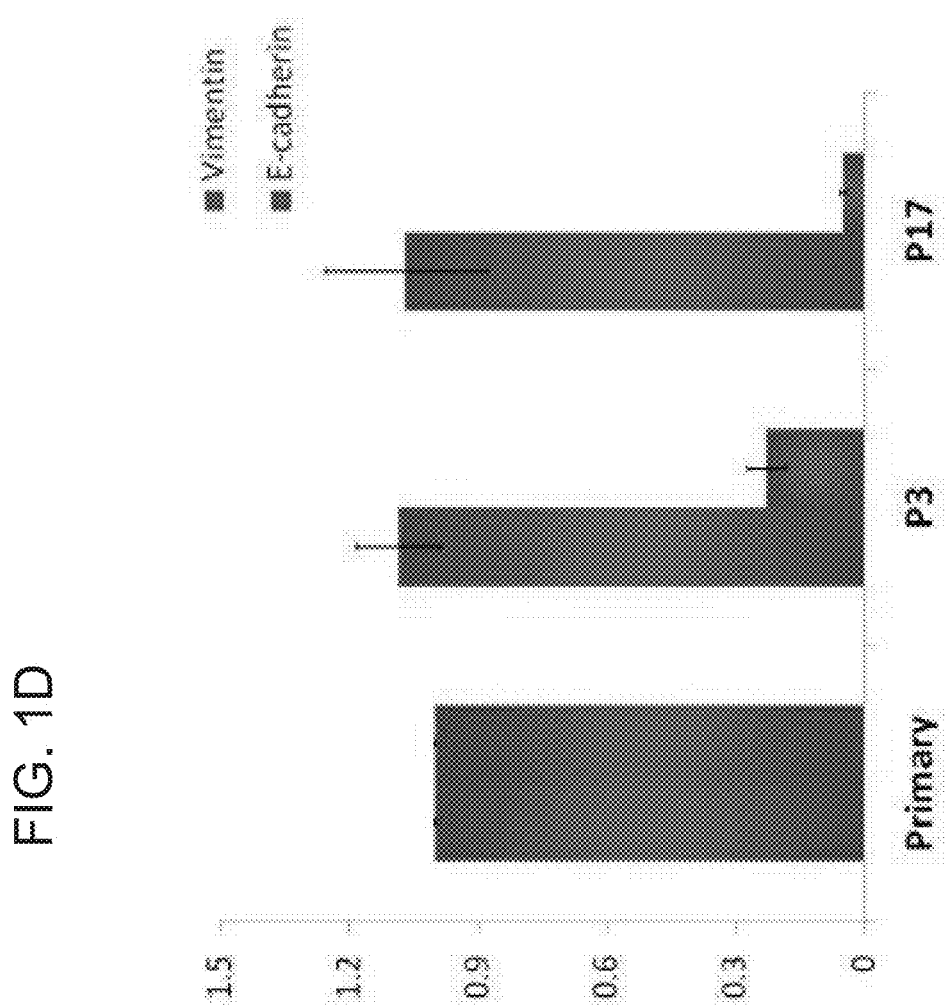

FIG. 2C

10 most up-regulated genes

| Gene | ID | Symbol | P2 vs P | P7 vs P | P17 vs P |
|---|---|---|---|---|---|
| CXCL6 | 1173001 | chemokine (C-X-C motif) ligand 6 | 12.2 | 119.4 | 287.0 |
| CXCL5 | 1172875 | chemokine (C-X-C motif) ligand 5 | 12.1 | 55.0 | 246.8 |
| SEMA3C | 1723808 | sema domain | 55.0 | 105.2 | 235.4 |
| GPM6A | 1730201 | glycoprotein M6A | 28.5 | 120.7 | 109.4 |
| FSTL5 | 1741926 | follistatin-like 5 | 10.2 | 110.8 | 138.9 |
| ALDH1A1 | 1741044 | aldehyde dehydrogenase 1 family, A1 | 23.7 | 100.8 | 130.4 |
| ANXA1 | 1171754 | annexin A1 | 41.9 | 63.3 | 115.0 |
| LOX | 1728200 | lysyl oxidase | 32.5 | 25.4 | 109.5 |
| DSE | 1730823 | dermatan sulfate epimerase-like | 14.0 | 39.6 | 97.6 |
| DLX2 | 1735181 | distal-less homeobox 2 | 5.7 | 4.6 | 76.0 |

10 most down-regulated genes

| Gene | ID | Symbol | P2 vs P | P7 vs P | P17 vs P |
|---|---|---|---|---|---|
| HBG1 | 1753868 | hemoglobin, gamma A | -363.1 | -381.3 | -403.4 |
| EBF3 | 1725867 | early B-cell factor 3 | -1.2 | 2.0 | -197.7 |
| HBB | 1171347 | hemoglobin, beta | -147.2 | -120.8 | -188.6 |
| SPP1 | 1727780 | secreted phosphoprotein 1 | 36.2 | -10.1 | -123.0 |
| CD163 | 1728679 | CD163 molecule | -87.4 | -96.3 | -102.5 |
| SDC2 | 1720763 | syndecan 2 | -1.5 | -12.4 | -94.1 |
| RNASE1 | 1716222 | ribonuclease, RNase A family, 1 | 69.7 | -86.5 | -82.3 |
| FBN | 1720338 | fin bud initiation factor homolog | -3.5 | -3.6 | -73.5 |
| SERPINB2 | 1719631 | serpin peptidase inhibitor clade B | -4.4 | -82.3 | -68.9 |
| SSTR1 | 1172804 | somatostatin receptor 1 | -0.7 | -8.1 | -68.4 |

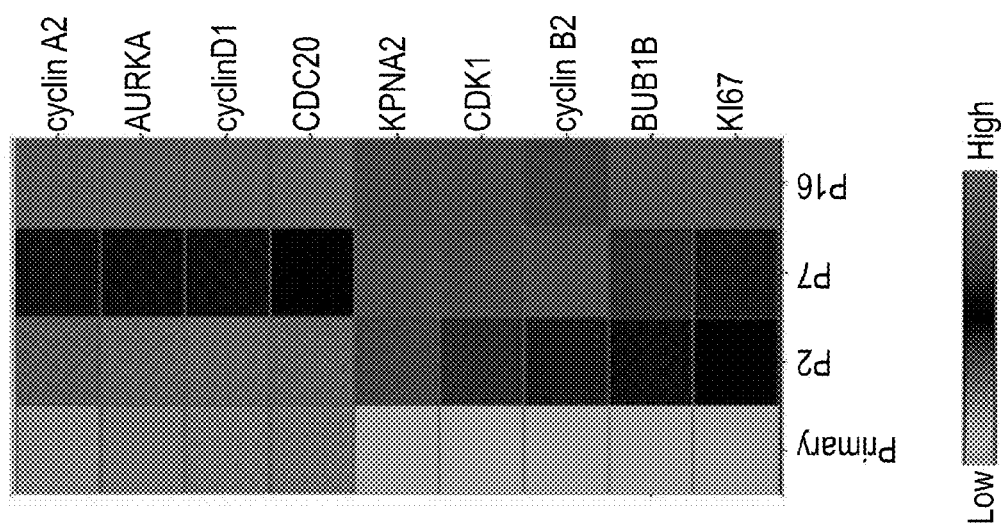

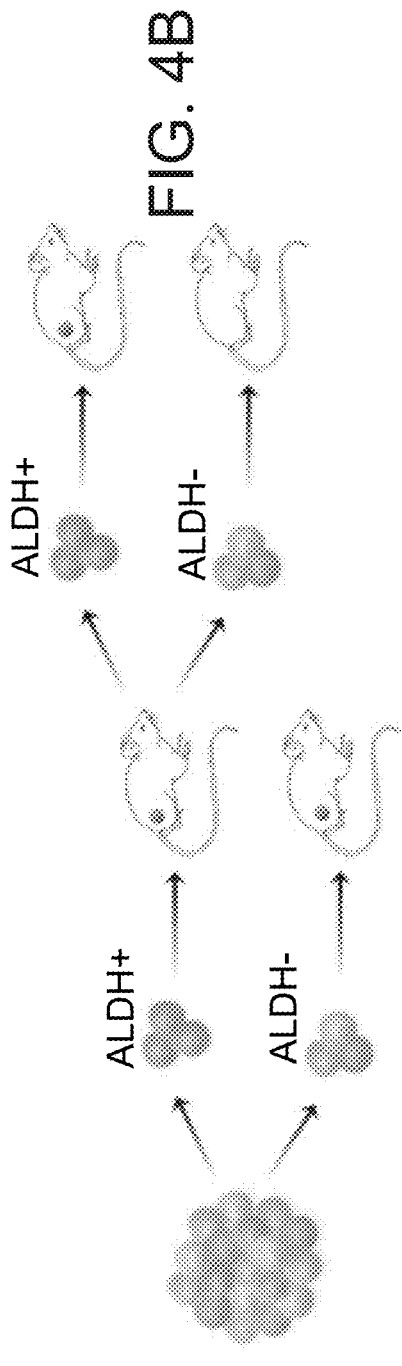
FIG. 4B
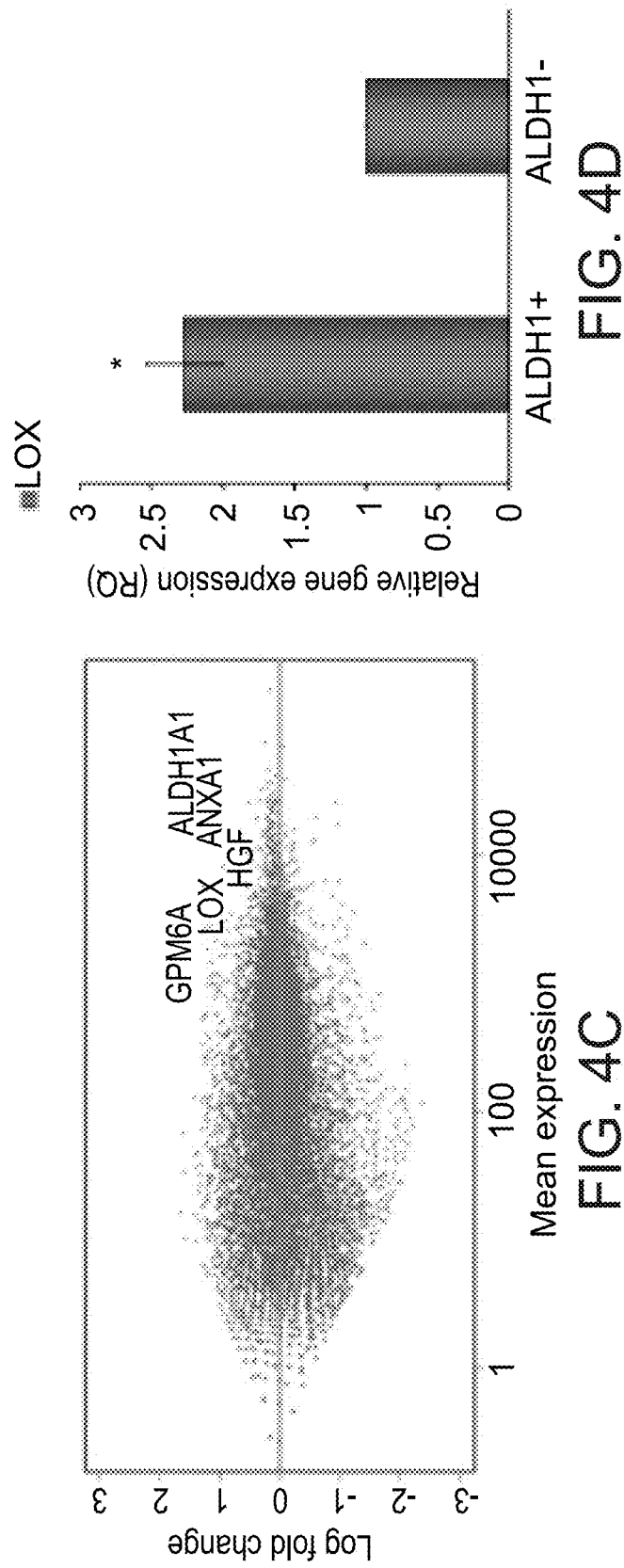
FIG. 4C
FIG. 4D

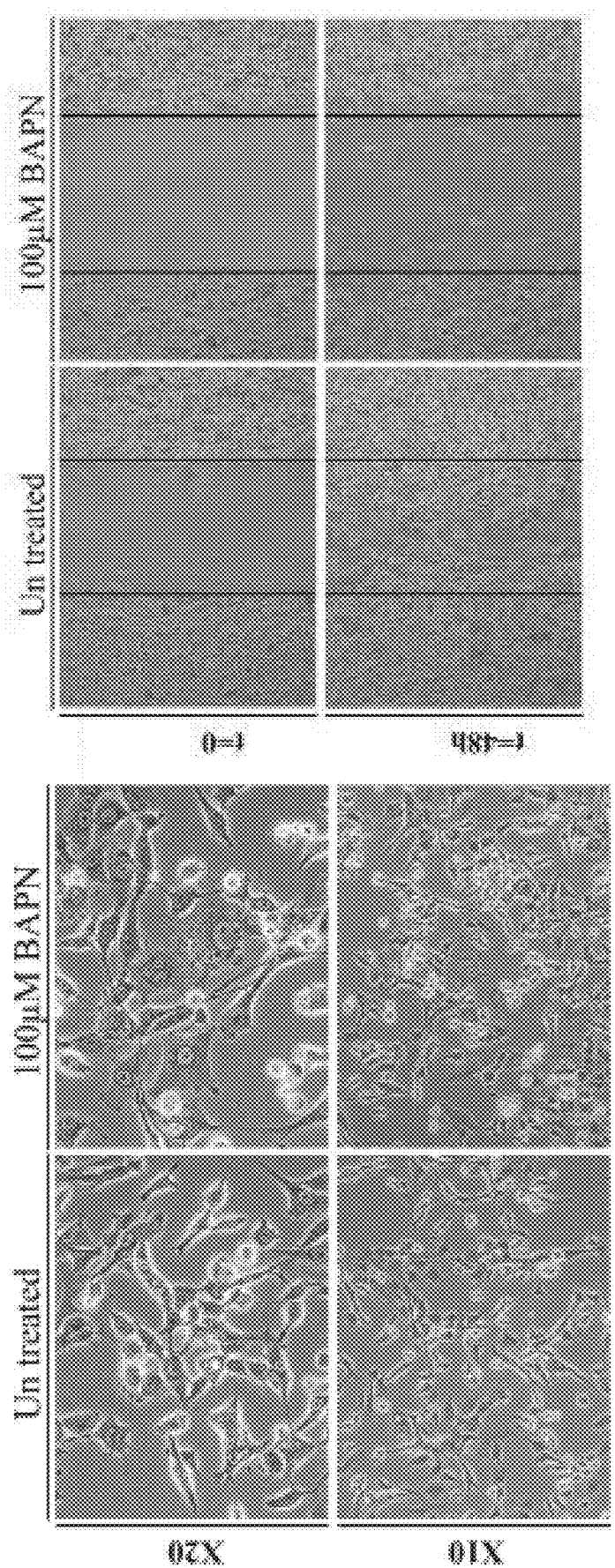

Ewing sarcoma

Wilm"s tumor

IDENTIFICATION OF CANCER STEM CELLS MARKERS AND USE OF SAME FOR DIAGNOSIS AND TREATMENT

RELATED APPLICATIONS

This application is a National Phase of PCT Patent Application No. PCT/IL2015/050663 having International filing date of Jun. 25, 2015, which claims the benefit of priority under 35 USC § 119(e) of U.S. Provisional Patent Application No. 62/016,773 filed on Jun. 25, 2014. The contents of the above applications are all incorporated by reference as if fully set forth herein in their entirety.

FIELD AND BACKGROUND OF THE INVENTION

The present invention, in some embodiments thereof, relates to methods of enriching and identifying cancer stem cells in primary tumors and optionally isolating therefrom. Markers which distinguish the cancer stem cells from the other cancer cells present in the primary tumor can then be identified in order to aid in diagnosis of the cancer. In addition, the markers may be targeted for the treatment of the cancer.

Recent years have witnessed the exciting discoveries of cancer-initiating/cancer stem cells (CSCs) in solid tumors. Applying principles established from stem cell research, human CSCs are functionally defined by their enriched capacity to regenerate cancers using xenograft (Xn) mouse models. Similar to normal stem cells, CSCs can reproduce themselves through the process of self-renewal, which can be studied in serial transplantation assays. Additionally, cancers derived from purified CSCs recapitulate the heterogeneous phenotypes of the parental cancer from which they were derived, reflecting the differentiation capacity of CSCs. Prospective isolation of CSCs has been performed based on surface marker expression, enabling the repeated isolation of highly purified populations of stem cells by flow cytometry prior to cell culture.

Malignant rhabdoid tumors are among the most aggressive and highly malignant embryonal tumors in young children. These tumors can occur in kidney (termed rhabdoid tumor), extra-renal tissues or the central nervous system (termed ATRT). They are characterized by an almost complete penetrance of loss of SMARCB1, a core component of the SWI/SNF chromatin remodeling complex located at region 11.2 of the long arm of chromosome 22 (22q11.2). Germline mutations were described and are correlated with very early age at diagnosis, synchronous and metachronous tumors at different locations and worst prognosis. Aberrant gene expression due to loss of SWI/SNF function is thought to play a major role in carcinogenesis, concordant with the important role of chromatin remodeling in cytokine signaling, differentiation, pluripotency and self-renewal. Despite optimized currently available medical care including surgery, chemotherapy and radiation, rhabdoid tumor maintains a very poor prognosis, with overall survival approximating 25%. To improve cure rates and to decrease short and long-term morbidity, continued expansion of our understanding of origins of tumors, development of models for tumor cancer interrogation, and the development of novel more tolerable biologically targeted therapies are necessary.

Background art includes Pode-Shakked et al., EMBO Molecular Medicine, Volume 5, Issue 1, pages 18-37, 2013 and Metildi et al, Cancer Res 2014; 74(19 Suppl): Abstract nr 4960. doi:10.1158/1538-7445.AM2014-4960.

SUMMARY OF THE INVENTION

According to an aspect of some embodiments of the present invention there is provided a method of identifying cancer stem cell markers in a human primary tumor comprising:
(a) in vivo passaging the primary tumor; and
(b) comparing a level of at least one antigen in a first population of passaged tumor cells of the primary tumor with a second population of tumor cells of the primary tumor, wherein the second population of tumor cells are:
(i) non-passaged cells of the human primary tumor; or
(ii) in vivo passaged cells of the human primary tumor, wherein the second population of tumor cells has been in vivo passaged for at least one less number of passages than the first population of passaged tumor cells,
wherein an increase in the amount of the antigen in the first population of tumor cells as compared to the amount of the antigen in the second population of tumor cells is indicative of a cancer stem cell marker in the human primary tumor.

According to an aspect of some embodiments of the present invention there is provided a method of treating a cancer in a subject in need thereof comprising administering to the subject a therapeutically effective amount of an agent which down regulates expression and/or inhibits an activity of an antigen, wherein the ratio of the amount of the antigen in in-vivo passaged cells of the tumor: the amount of the antigen in primary cells of the tumor is above a predetermined level. According to an aspect of some embodiments of the present invention there is provided a method of diagnosing a cancer in a subject, comprising analyzing a level of an antigen in a tumor of the subject, wherein the presence of the antigen is indicative of cancer, wherein the ratio of the amount of the antigen in in-vivo passaged cells of the tumor: the amount of the antigen in primary cells of the tumor is above a predetermined level.

According to an aspect of some embodiments of the present invention there is provided a method of monitoring a cancer treatment in a subject, comprising analyzing a level of an antigen in a primary tumor of the subject following administration of the cancer treatment, wherein a decrease in the amount of the antigen as compared to the level of the antigen prior to administration of the cancer treatment is indicative of a therapeutic treatment, wherein the ratio of the amount of the antigen in in-vivo passaged cells of the tumor of the subject: the amount of the antigen in primary cells of the tumor of the subject is above a predetermined level.

According to an aspect of some embodiments of the present invention there is provided a method of selecting an agent for the treatment of cancer in a subject:
(a) identifying at least one cancer stem cell marker in a primary tumor of the subject according to the method described herein; and
(b) selecting an agent which down regulates expression and/or inhibits an activity of the cancer stem cell marker, thereby selecting an agent for the treatment of cancer.

According to an aspect of some embodiments of the present invention there is provided a method of treating an atypical teratoid/rhabdoid tumor (ATRT) tumor in a subject in need thereof, comprising administering to the subject a therapeutically effective amount of an agent which binds to and/or downregulates expression of a polypeptide selected from the group consisting of semaphorin3C (SEMA3C), lysyl oxidase (LOX), glycoprotein M6A (GPM6A), hepatocyte growth factor (HGF/SF) and aldehyde dehydrogenasel (ALDH1), thereby treating ATRT.

According to an aspect of some embodiments of the present invention there is provided a method of monitoring a cancer treatment in a subject comprising:

(a) identifying at least one cancer stem cell marker in a primary tumor of the subject according to the method described herein;

(b) analyzing an amount of the cancer stem cell marker in the tumor of the subject following the cancer treatment, wherein a decrease in the amount of the cancer stem cell marker in the tumor as compared to the amount of the cancer stem cell marker prior to the treatment is indicative of an efficacious cancer treatment.

According to an aspect of some embodiments of the present invention there is provided a method of diagnosing cancer in a subject comprising identifying at least one cancer stem cell marker in a biological sample of the subject according to the method described herein, wherein the presence of the cancer stem cell marker is indicative of the cancer.

According to some embodiments of the invention, the number of passages of the first population of passaged cells is selected such that there is an apparent tumor aggressiveness phenotype which is not significantly increased for at least two consecutive passages.

According to some embodiments of the invention, the number of passages of the first population is selected such that the frequency of initiating a later generation xenograft using 5000 cells of the first population of passaged cells is increased by at least 5 fold as compared to non-passaged cells of the human primary tumor.

According to some embodiments of the invention, the number of passages of the first population of passaged cells is selected such that the ratio of cancer stem cells: non cancer stem cells in the first population of passaged cells is greater than 1:1000.

According to some embodiments of the invention, the antigen is a polypeptide.

According to some embodiments of the invention, the increase in the amount of the polypeptide is an increase in a level of expression of the polypeptide per cell.

According to some embodiments of the invention, the increase in the amount of the polypeptide is an increase in an amount of cells expressing the polypeptide.

According to some embodiments of the invention, the increase in the amount of the polypeptide is an increase in a level of expression of the polypeptide per cell and an increase in an amount of cells expressing the polypeptide.

According to some embodiments of the invention, the cancer stem cell frequency in the first population of tumor cells: cancer stem cell frequency in the second population of tumor cells is greater than 5:1.

According to some embodiments of the invention, the primary tumor is a pediatric tumor.

According to some embodiments of the invention, the primary tumor is selected from the group consisting of atypical teratoid/rhabdoid tumor (ATRT), Ewings's sarcoma, Angiomyolipoma. Pleuropulmonary Blastoma and Wilms' tumor.

According to some embodiments of the invention, the first population of passaged tumor cells are passaged for a minimum of 2 passages.

According to some embodiments of the invention, the second population of tumor cells are sequentially passaged in vivo for no more than 5 passages.

According to some embodiments of the invention, the first population of passaged tumor cells are passaged in vivo for at least 5 passages.

According to some embodiments of the invention, the passaging is effected in mice.

According to some embodiments of the invention, the passaging is effected by implanting into an animal non-dissociated cells of a tissue sample of a xenograft of the primary tumor.

According to some embodiments of the invention, the passaging is effected by implanting into an animal a single cell suspension of a xenograft of the primary tumor.

According to some embodiments of the invention, the determining the expression of the at least one polypeptide is effected on the mRNA level.

According to some embodiments of the invention, the determining the expression of the at least one polypeptide is effected on the protein level.

According to some embodiments of the invention, the cancer cell aggressiveness phenotype is selected from the group consisting of a level of a cancer cell marker, a gene expression profile, a time for xenograft to take, a number of cells required for generation of xenograft, an ability to migrate, an ability to invade non-cancerous tissue and a level of proliferation.

According to some embodiments of the invention, the first population of tumor cells has not undergone immunoisolation.

According to some embodiments of the invention, the antigen is a cancer stem cell marker identified according to the method described herein.

According to some embodiments of the invention, the antigen is a polypeptide.

According to some embodiments of the invention, the ratio of expression of the polypeptide in the primary tumor: expression of the polypeptide in the in-vivo passaged cells is at least 1:5.

According to some embodiments of the invention, the in-vivo passaged cells comprise cells which have undergone at least 3 in-vivo passages.

According to some embodiments of the invention, the polypeptide is lysyl oxidase (LOX).

According to some embodiments of the invention, the agent is (β-Aminopropionitrile (BAPN).

According to some embodiments of the invention, when the cancer stem cell marker is selected from the group consisting of semaphorin3C (SEMA3C), lysyl oxidase (LOX), glycoprotein M6A (GPM6A), hepatocyte growth factor (HGF/SF) and aldehyde dehydrogenasel (ALDH1), the cancer is ATRT.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL
VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D. Long-term propagation of MRT is associated with an increase in CSC frequency (A) Serial Xn propagation correlated with shorter time to tumor engraftment (blue) and increase in weight to time to resection ratio (red), indicating change in tumor behavior towards more aggressive phenotype; (B) H&E staining of primary MRT, early passage Xn (P2), intermediate passage Xn (P7) and late passage Xn (P14). Xn tumors cells maintain the basic rhabdoid-like cellular morphology with some morphological differences including the acquisition of spindle like cells, vast areas of necrosis, less apoptotic bodies and more mitoses (white arrows). Scale bar, 100 µm (top) and 50 µm (bottom); (C) IHC of primary MRT, early passage Xn (P2), intermediate passage Xn (P7) and late passage Xn (P14) in serial sections for cytokeratin AE1/AE3, epithelial membrane antigen (EMA), neurofilament protein (NFP) and vimentin. High generation Xn showed loss of differentiation markers (top three panels) while primary tumor and Xn tissues strongly express vimentin (bottom panel). Scale bar, 200 µm; (D) qRT-PCR analysis comparing the expression levels of E-cadherin and vimentin between primary tumor, early passage Xn (P3) and late passage Xn (P17). The expression of the epithelial marker, E-cadherin, is down-regulated throughout serial propagation while the expression of vimentin remains permanent. For qRT-PCR analyses the values for primary tumor cells were used to normalize (therefore=1) and all other values were calculated with respect to them. Results are presented as the mean±S.E.M of three separated experiments. *$p<0.05$; (D) Representative flow cytometry analysis of Xn cells from low, intermediate and high MRT passages for the expression of several CSC markers including CD24, CD34, CD90, CD56, CD326 and ALDH1 antigens on single cell suspensions. The results revealed that ALDH1 is a good candidate for MRT CSC marker, presenting a pattern of increased expression through Xn passages.

FIGS. 2A-E. Global gene signature associated with enhanced tumor initiating activity reveals putative CSC biomarkers and a new therapeutic target. (A) Microarray gene expression analysis comparing several different samples: 1.primary MRT, 2. Early MRT Xn (P2), 3. Intermediate MRT Xn (P7), 4. Late MRT Xn (P17), 5. Human Embryonal Stem Cells (hESCs), 6. Fetal kidney (FK), 7. Adult kidney (AK), 8. Fetal brain (FB), 9. Adult brain (AB). Un-supervised hierarchical clustering revealed great similarity between MRT late passages and hESCs, emphasizing their un-differentiated nature; (B) comparison of the MRT tissues revealed two distinct gene expression patterns; genes that were up-regulated (red) and down-regulated (green) through-out the passages; (C) Ten most up-regulated genes associated with increased CSC function in MRT including semaphoring 3C (SEMA3C), lysyl oxidase (LOX), glycoprotein M6A (GPM6A), hepatocyte growth factor (HGF/SF) and aldehyde dehydrogenase1 (ALDH1); (D) Gene heat map comparing the expression pattern of several proliferation markers (e.g. K167, CDC20, CDK1 and CCNA2) between the different MRT samples, revealed that high passages are highly proliferative; (E) ingenuity© function analysis demonstrated decreased necrosis, cell death and differentiation of cells in high passages Xn compared to primary tumor and low passages Xn.

FIGS. 3A-E. ALDH1 is a putative marker for MRT CSC (A) Serial propagation of human MRT Xn in NOD/SCID mice results in enrichment of ALDH1 expressing cells, scheme; (B) Representative FACS analyses of different MRT Xn passages. As tumors progressed the proportion of ALDHA1 expressing cells significantly increased, 4% in cells derived from P4 (left) and 25% in cells derived from P10 cells (right), indicating an enrichment in ALDH1$^+$ expressing cells through Xn serial propagation; (C) IHC of primary MRT, intermediate passage Xn (P7) and late passage Xn (P13) for ALDH1 reveals increased expression with Xn serial propagation. Scale bar, 200 µm; (D) Large magnification IHC of primary MRT for ALDH1 demonstrating that high ALDH1 expressing cells are mainly large Rhabdoid cells. Scale bar, 200 µm; (E) Validation via qRT-PCR revealed high ALDH1 expression in late passages, about 40 times higher in comparison to primary tumor. For qRT-PCR analyses the values for primary tumor cells were used to normalize (therefore=1) and all other values were calculated accordingly. Results are presented as the mean±S.E.M of three separated experiments. *$p<0.05$; **$p<0.01$.

FIGS. 4A-D. Functional validation of ALDH1 as MRT CSC biomarker (A) Colony forming ability was compared between ALDH1+ and ALDH1– MRT cells. Number of colonies formed by ALDH1+ cells was significantly higher in comparison to ALDH1– cells (left top bar graph; p=0.0083). Number of cells/colony was significantly higher in ALD1+ compared to ALDH1– cells (left bottom bar graph; p=0.0024). Representative images of colonies formed from ALDH1+ and ALDH– cells are presented on the right. Experiments were performed in triplicates; (B) Tumors that arose from ALDH1+ cells could be further serially transplanted into secondary recipients, demonstrating in-vivo self-renewal capacity, consistent with the presence of tumor initiation capacity in this population; (C) RNA sequencing experiment demonstrate that among the most up-regulated genes in the ALDH+ cells in comparison to ALDH– cells were those significantly overexpressed genes in late Xn passages in comparison to the primary tumor (e.g. ANXA1, GPM6A, HGF and LOX). (D) Validation via qRT-PCR revealed high LOX expression in sorted ALDH+ in comparison to ALDH– cells. For qRT-PCR analyses the values for ALDH– cells were used to normalize (therefore=1) and all other values were calculated accordingly. Results are presented as the mean±S.E.M of three separated experiments; *$p<0.05$.

FIGS. 5A-D. Functional validation of LOX inhibitor as a possible MRT therapeutic target (A) IHC staining of primary tumor, early (P2), intermediate (P7) and late (P14) MRT passages for LOX. The staining revealed a wide, increasing expression along Xn serial propagation. Scale bar, 100 µm; (B) The effect of BAPN on Wilms' tumor (WT) Xn cells, a common pediatric solid tumor of the kidney that was serial propagated in mice. The results demonstrated no effect on WT cell proliferation, indicating a specific effect of LOX inhibition on MRT cells. **$p<0.01$; (C) BAPN treatment induced morphological changes on MRT cells, including nuclear condensation and cell swallowing. Scale bar, 100 µm (top) and 50 µm (bottom); (D) Migration assay revealed that 100 µM BAPN treatment for 48 h significantly inhibited MRT cell's migration capacity, as compared to un-treated cells. Scale bar, 1000 µm.

Figure 6:
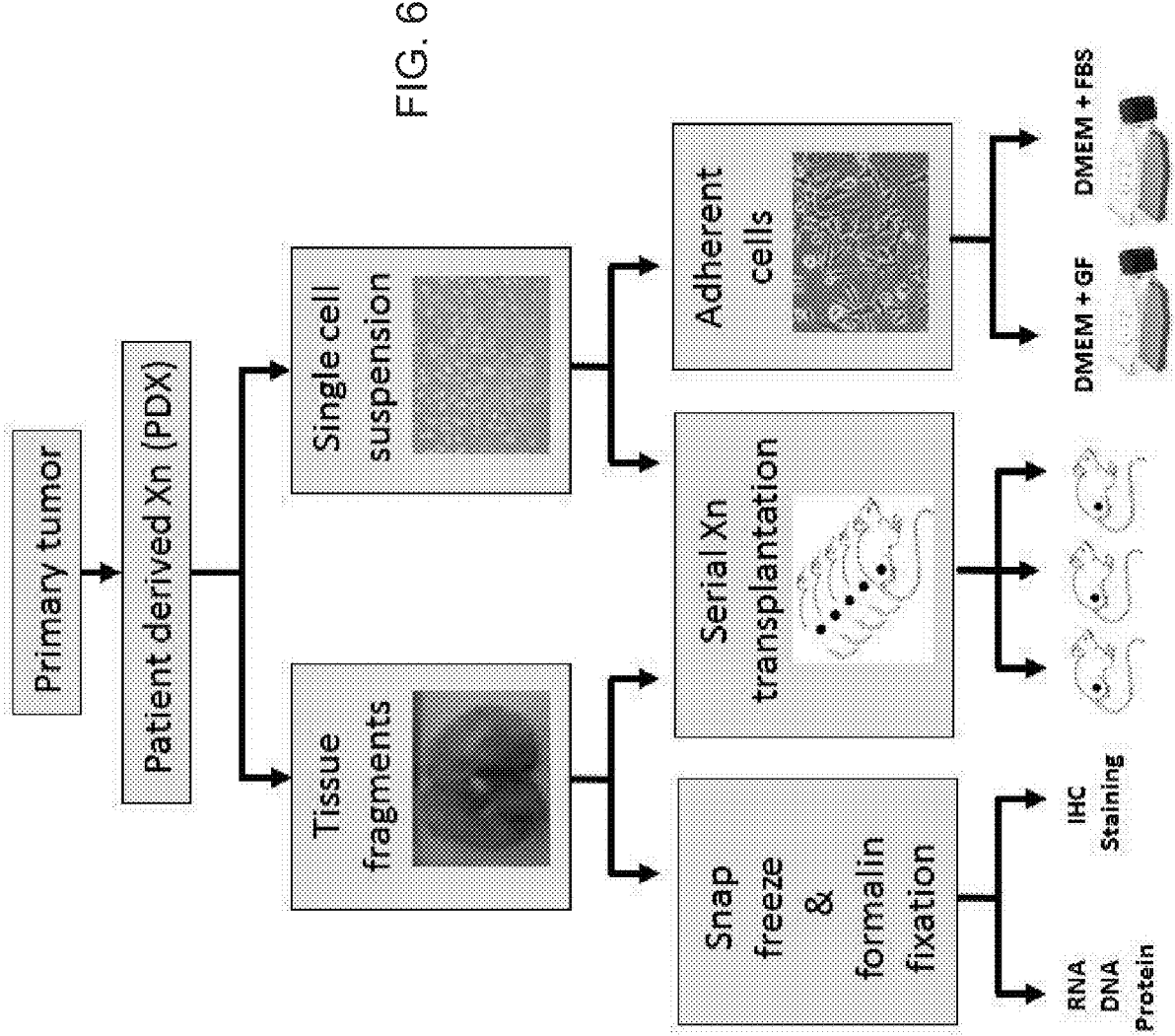

FIG. 6. Establishment of the ATRT Xn model, scheme. Primary tumor grafts were formed by a subcutaneous transplantation of 2-5 mm tumor pieces into immunodeficient mice. Tumor take was observed in all mice allowing tumor propagation. Sequential propagation of ATRT Xn in NOD/SCID mice was performed by tissue samples transplantation or single cell suspensions grafting utilizing a fixed number of $1\times10^6$ cells. Serial propagation allowed us to establish low (<P5), medium (P5-P10) and high-passage (P10-P15) ATRT Xn passages. Tissue fragments were also used for IHC staining, RNA, DNA and protein isolation. Adherent cells were also used for in vitro studies of the tumor's cells.

FIGS. 7A-D. Functional validation of LOX inhibitor as ATRT CIC/CSC therapeutic agent (A) Cell viability assay following treatment. An MTS analysis, examining cell viability, was performed on P2 Xn cells grown with different concentration of BAPN (10-1000f μM) for 48 h. The treatment resulted with significantly reduced proliferation (47% in comparison to UT cells) following treatment with 100 μM BAPN. **, $p<0.01$. (B) BAPN treatment induced morphological changes on ATRT cells. Among the changes observed following treatment are: nuclear condensation and cell swallowing. Scale bar, 100 μm (top) and 50 μm (bottom). (C) BAPN treatment inhibits cell migration. Migration assay revealed that 100 μM BAPN treatment for 48 h significant inhibited ATRT cell's migration capacity, as compared to un-treated cells. Scale bar, 1000 μm. (D) BAPN effectively inhibits lox activity in ATRT cells. LOX activity quantification kit shows significant inhibition following treatment with 100 μM BAPN on P3 and P10 cells (81% and 63% respectively).

Figure 8A:
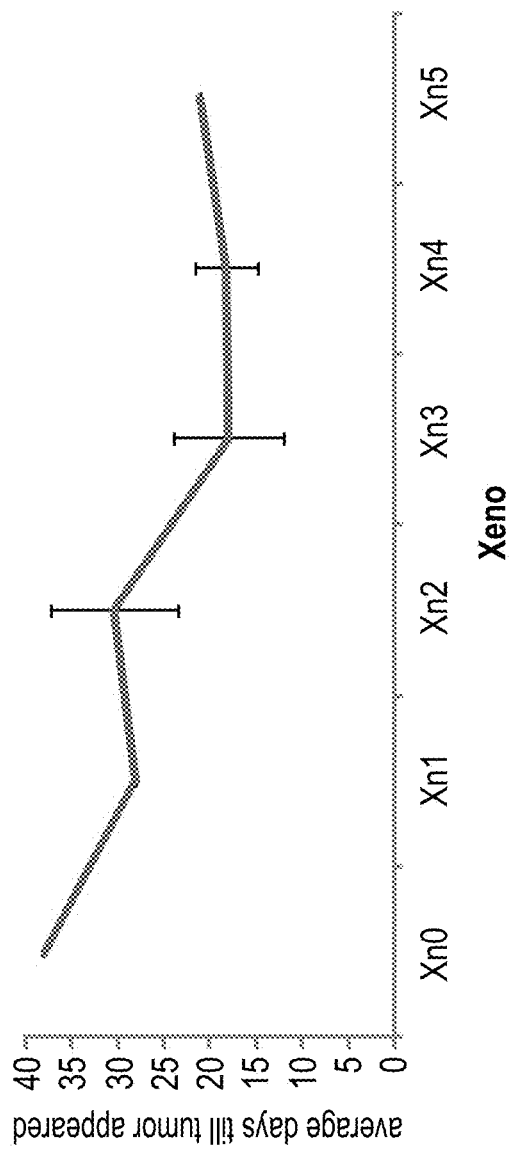
Figure 8B:
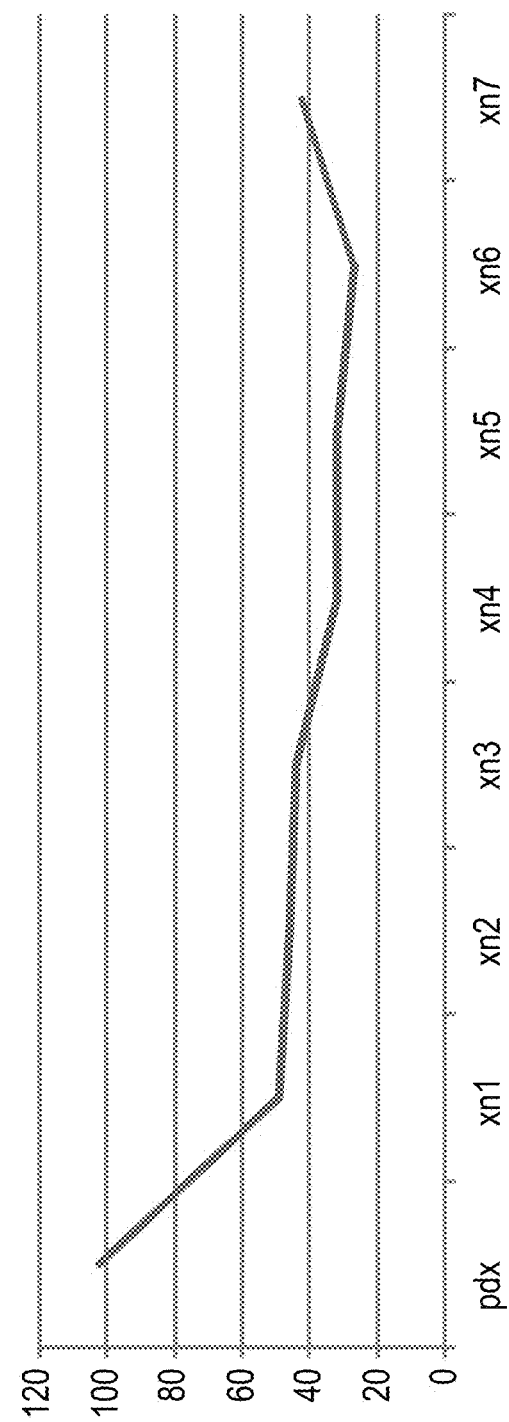

FIGS. 8A-B are graphs of average days until tumor appeared as a function of xenograft passage. Serial Xn propagation correlated with shorter time to tumor engraftment in both Ewing sarcoma (FIG. 8A) and Wilms tumor (FIG. 8B), indicating changes in tumor behavior towards a more aggressive phenotype.

Figure 9:
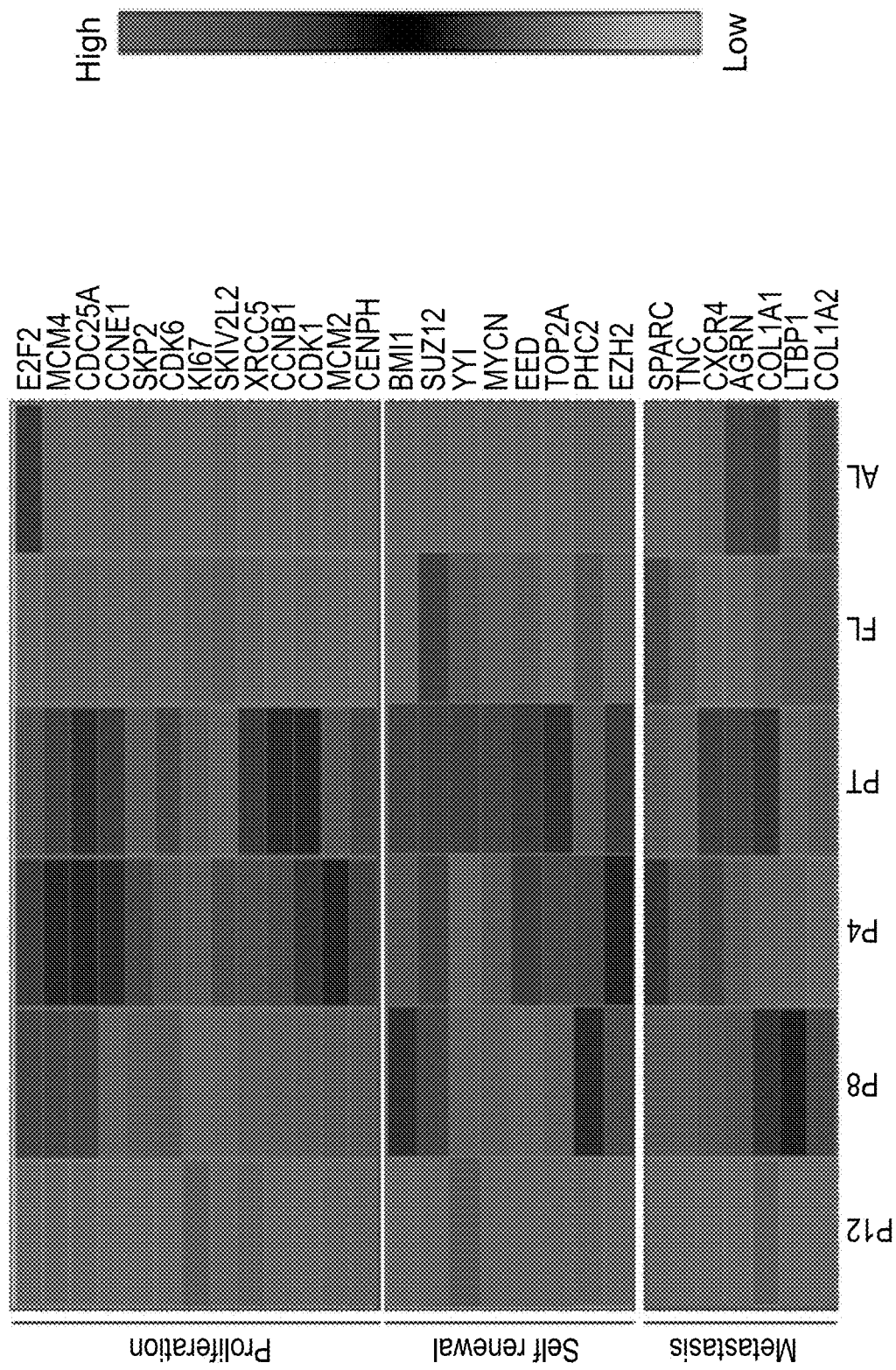

FIG. 9 is a gene heat map revealing later passages of tumor xenograft as highly proliferative, presenting up-regulation of self renewal genes, with an invasive gene signature, predicting metastatic behavior.

Figure 10A:
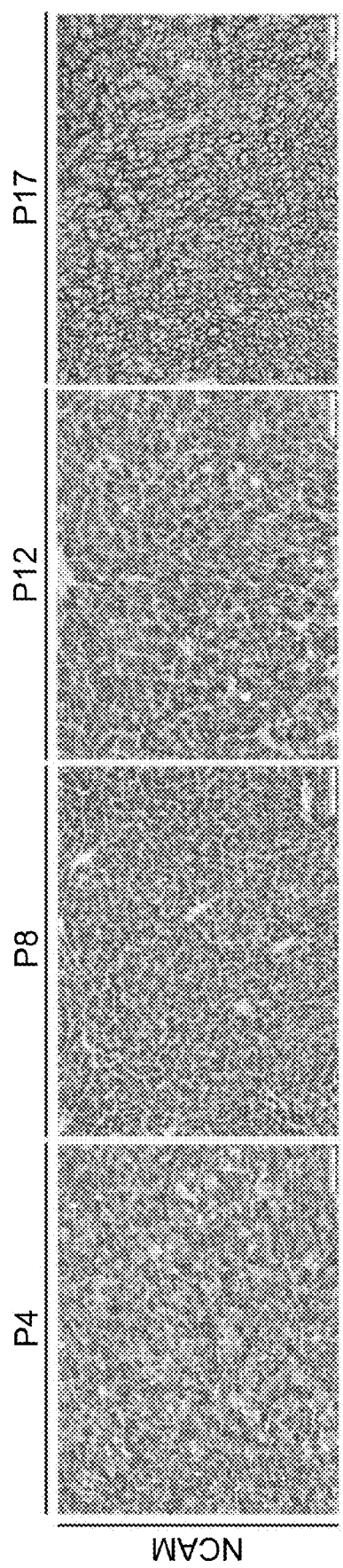
Figure 10B:
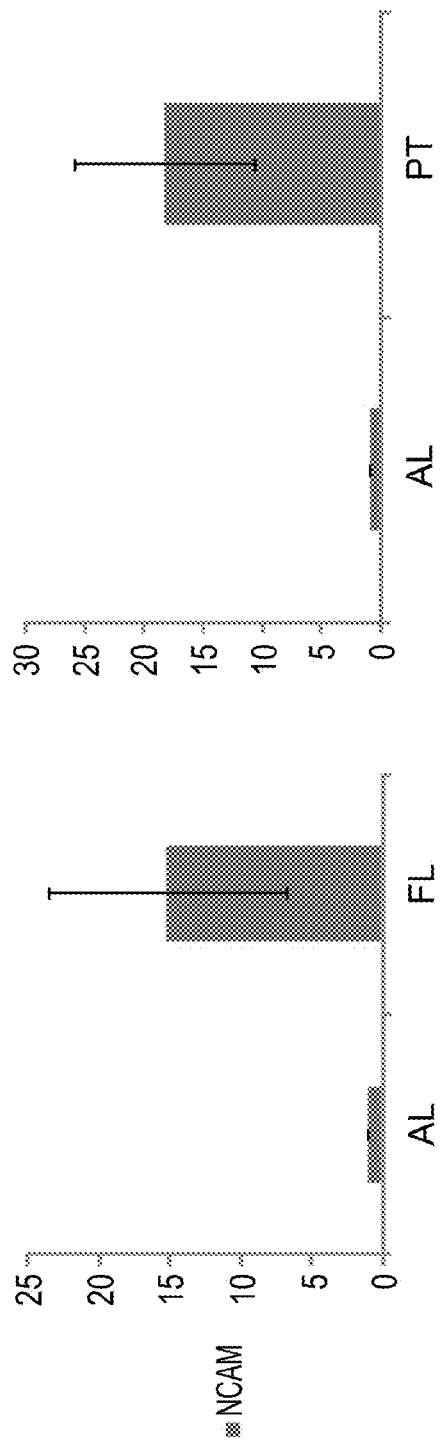

FIG. 10A—Immunohistochemistry (IHC) of several Xn passage (P4, P8, P12 and P17) for NCAM1 reveals increased expression with Xn serial propagation. Scale bar, 200 μm;

FIG. 10B—qRT-PCR analysis revealed high NCAM1 expression in the primary tumor in comparison to adult lung control (right) and high NCAM1 expression in fetal lung in comparison to adult lung (left). Results are presented as the mean±S.E.M of three separated experiments. *, $p<0.05$.

Figure 11A:
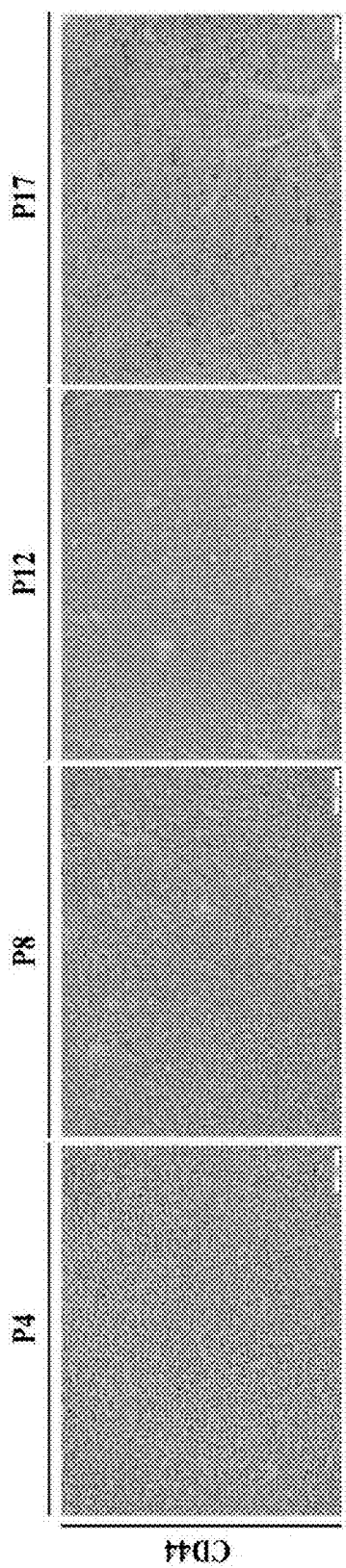
Figure 11B:
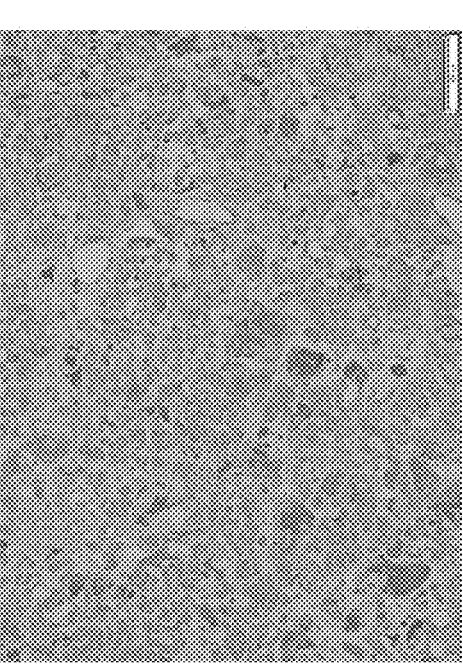

FIG. 11A—IHC of several Xn passage (P4, P8, P12 and P17) for CD44 reveals increased expression with Xn serial propagation. Scale bar, 200 μm;

FIG. 11B—Large magnification IHC of primary PPB for CD44 demonstrating that high CD44 expressing cells are scattered along the tumor. Scale bar, 200 μm.

DESCRIPTION OF SPECIFIC EMBODIMENTS OF THE INVENTION

The present invention, in some embodiments thereof, relates to methods of enriching and identifying cancer stem cells in primary tumors and optionally isolating therefrom. Markers which distinguish the cancer stem cells from the other cancer cells present in the primary tumor can then be identified in order to aid in diagnosis of the cancer. In addition, the markers may be targeted for the treatment of the cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Cancer stem cells (CSC) represent malignant cell subsets in hierarchically organized tumors, which are selectively capable of tumor initiation and self-renewal and give rise to bulk populations of non-tumorigenic cancer cell progeny through differentiation.

As a corollary to observations of a drug-resistant phenotype of physiological stem cells, it had been hypothesized that CSC might also represent a subpopulation within cancers that are characterized by increased resistance to chemo- and radiotherapy. Thus, cancer treatments that target CSC through specific markers could potentially increase the efficacy of current forms of therapy, by reducing the risk of relapse and dissemination. Identification of cancer stem cells is a complex task especially in view of the fact that they are typically expressed in very low numbers in the tumor cells.

In pediatric solid tumors, the limited access to multiple fresh tumor specimens compounds this problem, further impeding robust CSC analysis and efficient development of novel therapeutic strategies.

The present inventors combined long-term in vivo propagation of a human atypical teratoid/rhabdoid tumor (ATRT), a highly aggressive and lethal pediatric neoplasm, with limiting dilution xenotransplantation in immunodeficient mice to discover CSC phenotypes. Using this method, the present inventors were able to generate ATRT using as few as 50 cells, 40-fold less compared to low-passage xenografts.

The present inventors deduced from these experiments that sequential cycles of xenotransplantation may be used to select for additional CSC phenotypes and that this method may be a valuable tool for both cancer diagnosis and treatment.

Similarly to the ATRT, the present inventors showed that sequential propagation of Ewing's sarcoma, Wilm's tumor and pleuropulmonary blastoma (PPB) generated xenografts (Xns) which correlated with shorter time to tumor engraftment and accelerated tumor growth indicating the promotion of tumor aggressiveness along passages. Accordingly, the present inventors deduce that identification of CSCs may be carried out on multiple cancers using the above described methods.

Knowledge of the CSCs for a particular tumor aid in the development of new treatments. This may be effected on the personalized level (i.e. looking at CSCs in a tumor of a particular subject and treating accordingly) or on a more general level (development of therapeutics for particular cancers).

According to an aspect of the present invention there is provided a method of identifying cancer stem cell markers in a human primary tumor comprising:

(a) in vivo passaging the primary tumor for a number of passages to generate a first population of passaged tumor cells; and (b) comparing a level of at least one antigen in the first population of passaged tumor cells of the primary tumor with a second population of tumor cells of the primary tumor, wherein the second population of tumor cells are:

(i) non-passaged cells of the human primary tumor; or (ii) in vivo passaged cells of the human primary tumor, wherein the second population of tumor cells has been in vivo passaged for at least one less number of passages than the first population of passaged tumor cells, wherein an increase in the amount of the antigen in the first population of tumor cells as compared to the amount of the antigen in the second population of tumor cells is indicative of a cancer stem cell marker in the human primary tumor.

As used herein, the term "cancer stem cell", (also referred to as "CSC"), refers to a cell which has the capacity to regenerate cancers using xenograft (Xn) mouse models. CSCs can reproduce themselves through the process of self-renewal, which can be studied in serial transplantation assays. Additionally, cancers derived from purified CSCs recapitulate the heterogeneous phenotypes of the parental cancer from which they were derived, reflecting the differentiation capacity of CSCs.

As used herein, the term "tumor" refers to a group of cells or tissue that is formed by misregulated cellular proliferation. Tumors may show partial or complete lack of structural organization and functional coordination with the normal tissue, and usually form a distinct mass of tissue, which may be either benign or malignant. In one embodiment, the term tumor refers to a malignant tumor. According to one embodiment, the term "tumor cells" also comprises cells of non-solid cancers such as leukemia cells. According to another embodiment, respective cells of non-solid cancers are not encompassed by the term "tumor cells".

According to a specific embodiment the tumor is a solid tumor (e.g., pediatric) having an embryonic stem cell origin.

Examples of such solid tumors include, but are not limited to, sarcomas and carcinomas such as, but not limited to: fibrosarcoma, myxosarcoma, pleuropulmonary blastoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Examples of pediatric solid tumors include but are not limited to: Wilms' tumor/Nephroblastoma, rhabdomyosarcoma, Ewing's family of tumors/primitive neuroectodermal tumor, Osteosarcoma, peripheral neuroectodermal tumors, Childhood Germ Cell Tumor, Extragonadal Germ Cell Tumor, Kidney Cancer, Liver Cancer, Neuroblastoma, Ovarian Cancer, Retinoblastoma, Sarcoma, more specifically, Osteosarcoma, Rhabdomyosarcoma, Desmoplastic small round-cell tumor, Hepatoblastoma, Germ cell tumors, neuroblastoma and Medulloblastoma.

The phrase "primary tumor" as used herein refers to cells obtained from the anatomical site where tumor progression began and proceeded to yield a cancerous mass.

The antigen may be any molecule which is present in a differential amount in the CSC when compared to cancer cells of the same tumor which do not have the capacity to regenerate cancers using xenograft (Xn) mouse models and which cannot reproduce themselves through the process of self-renewal.

Thus, for example the CSC marker may be a polypeptide, a carbohydrate, a peptide, or an RNA molecule.

The antigen may be situated on the surface of the cell or may be an intracellular molecule.

According to a particular embodiment, the CSC marker is a polypeptide.

The polypeptide may be a cell surface protein (i.e. membrane protein). According to a particular embodiment, the cell surface protein is a carbohydrate binding molecule (e.g. lectin).

According to another embodiment, the protein is an intracellular protein (e.g. a soluble protein).

The polypeptide may serve a function e.g. a transcription factor, a pathway related marker etc.

As used herein, the phrase "in vivo passaging" refers to the process which includes initial implantation of the primary tumor into an animal (e.g. a mouse), waiting a period of time until the secondary tumor develops, harvesting the tumor cells and implanting those tumor cells into a second animal (i.e. serial transplantations). Subsequent sequential passages can then be carried out. The present invention contemplates passaging for at least one passage, at least two passages, at least three passages, at least four passages, at least five passages, at least six passages, at least seven passages, at least eight passages, at least nine passages and at least ten passages, at least eleven passages, at least twelve passages, at least thirteen passages, at least fourteen passages, at least fifteen passages, at least sixteen passages, at least seventeen passages, at least eighteen passages, at least nineteen passages, at least twenty passages.

According to a particular embodiment, the passaging is for 5 or more passages, for example between 5-30 passages, or 5-20 passages.

According to a particular embodiment, the passaging is for 10 or more passages, for example between 10-30 passages, or for 10-20 passages.

According to a particular embodiment, the tumor cells (the first population of tumor cells and/or the second population of tumor cells) have not undergone in vitro passaging.

According to still another embodiment, the tumor cells have not undergone more than one round of in vitro passaging.

Examples of animals which are used for the in vivo passaging include nematodes, fruit flies, zebrafish; preferably a laboratory mammal such as a mouse (nude mouse, SCID mouse, NOD/SCID mouse, Beige/SCID Mouse), rat, rabbit, or primate (e.g. humans) is used. According to one embodiment, immunodeficient animals are used. According to another embodiment, humans are used for the in-vivo passaging.

Typically, the same species of animal is used in each of the in vivo passages. Thus, for example, if immunodeficient mice are used for initial implantation, then immunodeficient mice are used for the subsequent passaging.

Any amount of primary tumor may be implanted so long as it initiates secondary tumor development in the second animal. According to a particular embodiment the primary tumor is cut into pieces (e.g. 1-10 mm pieces). Preferably, the cells of the primary tumor are not dissociated using an enzyme. In addition, the cells of the primary tumor are preferably not minced or ground.

According to a particular embodiment, the cells of the primary tumor have not undergone a round of purification (e.g. immune-isolation, such as by flow cytometry using an antibody which specifically binds to NCAM) prior to the implanting. Further, the cells of the xenografts in subsequent in vivo passages have preferably also not undergone a round of purification (e.g. immune-isolation, such as by flow cytometry, such as using an antibody which specifically binds to NCAM).

The tumor may be implanted in any way in the animal so long as it initiates tumor development. According to one embodiment, the tumor is implanted subcutaneously.

Typically, tumors are harvested approximately 1-3 months post implantation or when they reached a size of 1-3 cm e.g. 1.5 cm diameter.

Subsequent xenograft propagation may be effected by implanting single cell suspensions of the xenograft or pieces of the xenograft tissue.

For single cell suspensions, the number of dissociated cells will depend on the animal used in the in vivo passaging and the aggressiveness of the tumor. Typically about $0.5\text{-}3\times 10^6$ dissociated cells from freshly retrieved Xn tissue are used.

Pieces of xenograft tissue are typically between 1-10 mm, more preferably between 2-5 mm.

Single cells suspensions may be obtained by mincing, grinding or dispersing in the appropriate medium (preferably also containing antibiotics), followed by treatment with a protease enzyme such as collagenase. Enzymatically treated tissue may then be triturated in an appropriate medium.

According to a particular embodiment, the second population of tumor cells are non-passaged cells of the human primary tumor. According to another embodiment, the second population of tumor cells have undergone one round of passaging. According to another embodiment, the second population of tumor cells have undergone two rounds of passaging. According to another embodiment, the second population of tumor cells have undergone three rounds of passaging. According to another embodiment, the second population of tumor cells have undergone four rounds of passaging. According to another embodiment, the second population of tumor cells have not undergone more than five rounds of passaging.

The first population of tumor cells have at least undergone one round of in vivo passaging. According to another embodiment, the first population of tumor cells have undergone at least two rounds of in vivo passaging. According to another embodiment, the first population of tumor cells have undergone at least three rounds of in vivo passaging. According to another embodiment, the first population of tumor cells have undergone at least four rounds of in vivo passaging. According to another embodiment, the first population of tumor cells have undergone at least five rounds of in vivo passaging. According to another embodiment, the first population of tumor cells have undergone at least six rounds of in vivo passaging. According to another embodiment, the first population of tumor cells have undergone at least seven rounds of in vivo passaging. According to another embodiment, the first population of tumor cells have undergone at least eight rounds of in vivo passaging. According to another embodiment, the first population of tumor cells have undergone at least nine rounds of in vivo passaging. According to another embodiment, the first population of tumor cells have undergone at least ten rounds of in vivo passaging. According to another embodiment, the first population of tumor cells have undergone at least fifteen rounds of in vivo passaging. According to another embodiment, the first population of tumor cells have undergone at least twenty rounds of in vivo passaging.

Typically, the first population of tumor cells have undergone sufficient in vivo passaging such that the frequency of initiating a later generation xenograft using 5000 cells of said first population of passaged cells is increased by at least 5 fold as compared to non-passaged cells of the human primary tumor.

As used herein, the term "xenograft" refers to the surgical transplant or graft of tissue or organs from an individual of one species, genus or family into an individual of another species, genus, or family.

Preferably, the frequency of initiating a later generation xenograft is determined in at least 2 animals, e.g. 3 animals, 5 animals or more preferably even 10 animals such that a statistically significant number is attained.

Thus, by way of example, if the second population of tumor cells initiates a later generation xenograft in 1 out of 10 mice tested, the first population of tumor cells should undergo sufficient in vivo passaging such that a later generation xenograft is initiated in at least 5 out of 10 mice using the same number of tumor cells. Typically, the tumor cells which are used to initiate the later generation xenograft are in a single cell suspension.

Testing whether a later generation xenograft has been initiated is within the expertise of a person skilled in the art. Exemplary methods which may be used to determine whether a xenograft has initiated include gross tumor palpation, calipers, ultrasound-guided imaging, etc.

According to one embodiment, the first population of tumor cells have undergone sufficient in vivo passaging such that the frequency of initiating a later generation xenograft using 5000 cells of said first population of passaged cells is increased by at least 10 fold as compared to non-passaged cells of the human primary tumor.

According to one embodiment, the first population of tumor cells have undergone sufficient in vivo passaging such that the frequency of initiating a later generation xenograft using 5000 cells of said first population of passaged cells is increased by at least 20 fold as compared to non-passaged cells of the human primary tumor.

According to one embodiment, the first population of tumor cells have undergone sufficient in vivo passaging such that the frequency of initiating a later generation xenograft using 1000 cells of said first population of passaged cells is increased by at least 5 fold as compared to non-passaged cells of the human primary tumor.

According to one embodiment, the first population of tumor cells have undergone sufficient in vivo passaging such that the frequency of initiating a later generation xenograft using 1000 cells of said first population of passaged cells is increased by at least 10 fold as compared to non-passaged cells of the human primary tumor.

According to one embodiment, the first population of tumor cells have undergone sufficient in vivo passaging such that the frequency of initiating a later generation xenograft using 1000 cells of said first population of passaged cells is increased by at least 20 fold as compared to non-passaged cells of the human primary tumor.

According to one embodiment, the first population of tumor cells have undergone sufficient in vivo passaging such that the frequency of initiating a later generation xenograft using 500 cells of said first population of passaged cells is increased by at least 5 fold as compared to non-passaged cells of the human primary tumor.

According to one embodiment, the first population of tumor cells have undergone sufficient in vivo passaging such that the frequency of initiating a later generation xenograft using 500 cells of said first population of passaged cells is increased by at least 10 fold as compared to non-passaged cells of the human primary tumor.

According to one embodiment, the first population of tumor cells have undergone sufficient in vivo passaging such that the frequency of initiating a later generation xenograft using 500 cells of said first population of passaged cells is increased by at least 20 fold as compared to non-passaged cells of the human primary tumor.

According to one embodiment, the first population of tumor cells have undergone sufficient in vivo passaging such that the frequency of initiating a later generation xenograft using 100 cells of said first population of passaged cells is increased by at least 5 fold as compared to non-passaged cells of the human primary tumor.

According to one embodiment, the first population of tumor cells have undergone sufficient in vivo passaging such that the frequency of initiating a later generation xenograft using 100 cells of said first population of passaged cells is increased by at least 10 fold as compared to non-passaged cells of the human primary tumor.

According to one embodiment, the first population of tumor cells have undergone sufficient in vivo passaging such that the frequency of initiating a later generation xenograft using 100 cells of said first population of passaged cells is increased by at least 20 fold as compared to non-passaged cells of the human primary tumor.

According to one embodiment, the first population of tumor cells have undergone sufficient in vivo passaging such that the frequency of initiating a later generation xenograft using 50 cells of said first population of passaged cells is increased by at least 5 fold as compared to non-passaged cells of the human primary tumor.

According to one embodiment, the first population of tumor cells have undergone sufficient in vivo passaging such that the frequency of initiating a later generation xenograft using 50 cells of said first population of passaged cells is increased by at least 10 fold as compared to non-passaged cells of the human primary tumor.

According to one embodiment, the first population of tumor cells have undergone sufficient in vivo passaging such that the frequency of initiating a later generation xenograft using 50 cells of said first population of passaged cells is increased by at least 20 fold as compared to non-passaged cells of the human primary tumor.

Typically, the first population of tumor cells have undergone one more round of passaging than the second population of tumor cells. According to another embodiment, the first population of tumor cells have undergone two more rounds of passaging than the second population of tumor cells. According to another embodiment, the first population of tumor cells have undergone three more rounds of passaging than the second population of tumor cells. According to another embodiment, the first population of tumor cells have undergone four more rounds of passaging than the second population of tumor cells. According to another embodiment, the first population of tumor cells have undergone five more rounds of passaging than the second population of tumor cells. According to another embodiment, the first population of tumor cells have undergone six more rounds of passaging than the second population of tumor cells. According to another embodiment, the first population of tumor cells have undergone seven more rounds of passaging than the second population of tumor cells. According to another embodiment, the first population of tumor cells have undergone eight more rounds of passaging than the second population of tumor cells. According to another embodiment, the first population of tumor cells have undergone nine more rounds of passaging than the second population of tumor cells. According to another embodiment, the first population of tumor cells have undergone ten more rounds of passaging than the second population of tumor cells. According to another embodiment, the first population of tumor cells have undergone more than ten more rounds of passaging than the second population of tumor cells.

In one embodiment, the first population of tumor cells has been passaged such that there is an apparent tumor aggressiveness phenotype which is not significantly increased for at least two consecutive passages.

It will be appreciated that during initial passaging, the rate of increase of a tumor aggressiveness phenotype is high. Over subsequent passaging, the rate of increase of a tumor aggressiveness phenotype slows down until at a particular passage, a plateau is reached. At this point the level of the tumor aggressiveness phenotype remains constant or may even be reduced over subsequent passages.

The present inventors contemplate passaging the tumor for a number of passages such that the tumor aggressiveness phenotype reaches a plateau. The change in tumor aggressiveness phenotype at the plateau is preferably no greater than 10%, 9%, 8%, 7%, 6%, 5%, 4%, 3%, 2%, or even 1%.

Examples of tumor aggressiveness phenotypes which may be measured according to this aspect of the present invention include, but are not limited to: a level of a cancer cell marker, a gene expression profile, a level of invasiveness, an ability to metastasize, a level of metastasis, a time for xenograft to take (i.e. a time for a xenograft to generate a tumor of a particular size in an animal model), a number of cells required for generation of xenograft of a particular size in an animal model). Additional tumor aggressiveness phenotypes which may be measured include chromosomal stability, kinase activity, cell adhesion, apoptosis, cancer cell growth, cyclin production, cell proliferation, cancer cell growth, measuring clonogenicity (soft agar assays), measuring anchorage-independent growth, measuring cell cycle regulation, measuring cancer cell motility, measuring angiogenesis, and measuring cell death, among others.

The measurements may be effected in vivo (i.e. in animal models) or in vitro (e.g. in cell cultures).

Cell proliferation assays include, without limitation, MTT assays (for example, the Vybrant® MTT Cell Proliferation Assay Kit (Invitrogen)); BrdU incorporation assays (for example, the Absolute-S SBIP assay (Invitrogen)); measuring intracellular ATP levels (commercial versions of the assay include ATPLite™-M, 1,000 Assay Kit (PerkinElmer) and ATP Cell Viability Assay Kit (BioVision)); DiOc18 assay, a membrane permeable dye (Invitrogen); Glucose-6-phosphate dehydrogenase activity assay (for example, the Vibrant cytotoxicity assay (Invitrogen)); measuring cellular LDH activity; and $^3$H-thymidine incorporation and the Cell Titer Glo Assay (Promega).

Cell-cycle progression can be assayed by bromodeoxyuridine (BRDU) incorporation. Such assays identify a cell population undergoing DNA synthesis by incorporation of BRDU into newly synthesized DNA. Newly-synthesized DNA may then be detected using an anti-BRDU antibody (Hoshino et al., 1986, int. J. Cancer 38, 369; Campana et al., 1988, J. Immunol. Meth. 107, 79), or by other means. Cell proliferation can also be assayed by phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem. 270: 20098-105). Cell proliferation can also be examined using $^{3H}$-thymidine incorporation (Chen, J., 1996, Oncogene 13:1395-403; Jeoung, J., 1995, J. Biol. Chem. 270:18367-73). This assay allows for quantitative characterization of S-phase DNA synthesis. In this assay, cells synthesizing DNA will incorporate $^{3H}$-thymidine into newly synthesized DNA. Incorporation can then be measured by standard techniques such as by counting of radioisotope in a scintillation counter (e.g., Beckman L S 3800 Liquid Scintillation Counter). Another proliferation assay uses the dye Alamar Blue (available from Biosource International), which fluoresces when reduced in living cells and provides an indirect measurement of cell number (Voytik-Harbin S L at al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available and include the Promega CellTiter 96™ AQueous Non-Radioactive Cell Proliferation Assay (Cat #G5421). Cell proliferation can also be assayed by colony formation in soft agar (Sambrook at al., Molecular Cloning, Cold Spring Harbor (1989)). Cell proliferation may also be assayed by measuring ATP levels as indicator of metabolically active cells. Such assays are commercially available and include Cell Titer-Glo™ ((Promega). Cell cycle proliferation can also be assayed by flow cytometry (Gray J W at al. (1986) Int J Radiat Biol Relat Stud Phys Chem Med 49:237-55). Cells may be stained with propidium iodide and evaluated in a flow cytometer to measure accumulation of cells at different stages of the cell cycle.

Another example of a tumor aggressiveness phenotype which may be measured is an ability to cross a barrier. Preferably the tumor cells are prevented from crossing a barrier. The barrier for the tumor cells may be an artificial barrier in vitro or a natural barrier in vivo. In vitro barriers include but are not limited to extracellular matrix coated membranes, such as Matrigel. Thus, the tumor cells can then be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378-383. Matrigel is a reconstituted basement membrane containing type IV collagen, laminin, heparan sulfate proteoglycans such as perlecan, which bind to and localize bFGF, vitronectin as well as transforming growth factor-.beta. (TGF-.beta.), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated herein by reference. An in vivo barrier refers to a cellular barrier present in the body of a subject.

Growth characteristics of the tumor may also serve as a tumor aggressiveness phenotype (e.g., population doubling capability, doubling time, passages to senescence), Gene expression profiling (e.g., gene chip arrays; polymerase chain reaction (for example, reverse transcriptase PCR, real time PCR, and conventional PCR)) may also be used to analyze a tumor aggressiveness phenotype.

Additional assays contemplated by the present invention are summarized in Pouliot N, Pearson H B, Burrows A. Investigating Metastasis Using In Vitro Platforms. In: Madame Curie Bioscience Database [Internet]. Austin (Tex.): Landes Bioscience; 2000—the contents of which is incorporated herein by reference.

Examples of cancer cell markers which are increased in correlation with tumor aggressiveness include proliferation markers (e.g. K167, E2F2, and CDK1), self renewal polycomb genes (e.g. BMI1, TOP2A, and EZH2), and metastasis signature genes (e.g. SPARC, CXCR4 and LTBP1).

It will be appreciated that performing the method according to this aspect of the present invention allows for enrichment of cancer stem cells in the first population of cancer cells with respect to the second population of cancer cells. The present invention contemplates an enrichment level of cancer stem cells by as more than 2 fold, 3, fold, 4 fold, 5 fold, 6 fold, 7 fold, 8 fold, 9 fold, 10 fold, 15 fold, 20 fold, 30 fold, 40 fold, 50 fold or even 100 fold.

The number of cancer stem cells in the second population of tumor cells may be less than 1 in 1000 cells of the tumor, less than 1 in 2000 cells of the tumor, less than 1 in 3000 cells of the tumor, less than 1 in 4000 cells of the tumor, less than 1 in 5000 cells of the tumor, less than 1 in 6000 cells of the tumor, less than 1 in 7000 cells of the tumor, less than 1 in 8000 cells of the tumor, less than 1 in 9000 cells of the tumor, less than 1 in 10,000 cells of the tumor.

The number of cancer stem cells in the first population of tumor cells is typically greater than 1 in 1000 cells of the tumor, 1 in 900 cells of the tumor, 1 in 800 cells of the tumor, 1 in 700 cells of the tumor, 1 in 600 cells of the tumor, 1 in 500 cells of the tumor, 1 in 400 cells of the tumor, 1 in 300 cells of the tumor, 1 in 200 cells of the tumor, 1 in 100 cells of the tumor or even 1 in 10 cells of the tumor.

Preferably, the ratio of cancer stem cells: non cancer stem cells (i.e. the frequency of cancer stem cells) in the first population of tumor cells is such that it is possible to detect markers by gene expression analysis with an acceptable signal: noise ratio. It will be appreciated that the increase in the amount of the antigen may be due to an increase in the amount of antigen per cell (e.g. expression level of a polypeptide per cell) and/or may be due to an increase in the frequency of cells which comprise the antigen (e.g. the number of cells that express the polypeptide).

The overall increase in the amount of the antigen in the first population of tumor cells as compared to the amount of the antigen in the second population of tumor cells is typically at least 2 fold, at least 3 fold, at least 4 fold or even at least 5 fold.

The increase in the frequency of cells which comprise the antigen may be a 2 fold increase, a 3 fold increase, 4 fold increase, 5 fold increase, 6 fold increase, 7 fold increase, 8 fold increase, 9 fold increase, 10 fold increase, 20 fold increase, 30 fold increase, 40 fold increase, 50 fold increase, 60 fold increase, 70 fold increase, 80 fold increase, 90 fold increase, 100 fold increase or greater.

Methods of analyzing for the expression of a protein are provided herein below. It will be appreciated that the method may be performed on the RNA level or the protein level.

Methods of Detecting the Expression Level of RNA

The expression level of the RNA in the cells of some embodiments of the invention can be determined using methods known in the arts.

Northern Blot analysis: This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR analysis: This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA in situ hybridization stain: In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the bound probe is detected using known methods. For example, if a radio-labeled probe is used, then the slide is subjected to a photographic emulsion which reveals signals generated using radio-labeled probes; if the probe was labeled with an enzyme then the enzyme-specific substrate is added for the formation of a colorimetric reaction; if the probe is labeled using a fluorescent label, then the bound probe is revealed using a fluorescent microscope; if the probe is labeled using a tag (e.g., digoxigenin, biotin, and the like) then the bound probe can be detected following interaction with a tag-specific antibody which can be detected using known methods.

In situ RT-PCR stain: This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

DNA microarrays/DNA chips: The expression of thousands of genes may be analyzed simultaneously using DNA microarrays, allowing analysis of the complete transcriptional program of an organism during specific developmental processes or physiological responses. DNA microarrays consist of thousands of individual gene sequences attached to closely packed areas on the surface of a support such as a glass microscope slide. Various methods have been developed for preparing DNA microarrays. In one method, an approximately 1 kilobase segment of the coding region of each gene for analysis is individually PCR amplified. A robotic apparatus is employed to apply each amplified DNA sample to closely spaced zones on the surface of a glass microscope slide, which is subsequently processed by thermal and chemical treatment to bind the DNA sequences to the surface of the support and denature them. Typically, such arrays are about 2×2 cm and contain about individual nucleic acids 6000 spots. In a variant of the technique, multiple DNA oligonucleotides, usually 20 nucleotides in length, are synthesized from an initial nucleotide that is covalently bound to the surface of a support, such that tens of thousands of identical oligonucleotides are synthesized in a small square zone on the surface of the support. Multiple oligonucleotide sequences from a single gene are synthesized in neighboring regions of the slide for analysis of expression of that gene. Hence, thousands of genes can be represented on one glass slide. Such arrays of synthetic oligonucleotides may be referred to in the art as "DNA chips", as opposed to "DNA microarrays", as described above [Lodish et al. (eds.). Chapter 7.8: DNA Microarrays: Analyzing Genome-Wide Expression. In: Molecular Cell Biology, 4th ed., W. H. Freeman, New York. (2000)].

Oligonucleotide microarray—In this method oligonucleotide probes capable of specifically hybridizing with the polynucleotides of some embodiments of the invention are attached to a solid surface (e.g., a glass wafer). Each oligonucleotide probe is of approximately 20-25 nucleic acids in length. To detect the expression pattern of the polynucleotides of some embodiments of the invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara, Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

Methods of Detecting Expression and/or Activity of Proteins

Expression and/or activity level of proteins expressed in the cells of the cultures of some embodiments of the invention can be determined using methods known in the arts.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In situ activity assay: According to this method, a chromogenic substrate is applied on the cells containing an active enzyme and the enzyme catalyzes a reaction in which the substrate is decomposed to produce a chromogenic product visible by a light or a fluorescent microscope.

In vitro activity assays: In these methods the activity of a particular enzyme is measured in a protein mixture extracted from the cells. The activity can be measured in a spectrophotometer well using colorimetric methods or can be measured in a non-denaturing acrylamide gel (i.e., activity gel). Following electrophoresis the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

Once cancer stem cell markers have been identified, the present inventors propose that such markers can be used for the isolation of cancer stem cells. Contemplated methods include centrifugation based methods, elutriation, density gradient separation, apheresis, affinity selection, panning, immunological-based systems such as fluorescence activated cell sorting (FACS); immunoaffinity exchange; non-optical cell sorting methods including magnetic cell sorting using antibody-coated magnetic particles that bind to a specific cell type to separate desired cells.

In addition, the present inventors contemplate targeting the CSC markers for the purpose of treatment.

Further, the present inventors propose analyzing for the presence and/or level of the markers for the purpose of diagnosis, determining an optimal treatment, monitoring treatment efficacy and/or staging.

Thus, according to another aspect of the present invention there is provided a method of diagnosing a cancer in a subject, comprising analyzing for the presence of an antigen in a tumor of the subject, wherein the presence of the antigen is indicative of cancer, wherein the ratio of the amount of the antigen in in-vivo passaged cells of the tumor: primary cells of the tumor is above a predetermined level.

As used herein the term "diagnosing" refers to categorizing a subject as having a cancer and includes classifying a cancer, determining a severity of cancer (grade or stage), monitoring cancer progression, forecasting an outcome of the cancer and/or prospects of recovery.

The methods of the invention are particularly useful in detecting the early stages of cancer in outwardly healthy individuals.

The subject may be a healthy animal or human subject undergoing a routine well-being check up. Alternatively, the subject may be at risk of having cancer (e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness).

The amount of the CSC will depend on the type of cancer and the stage. In some embodiments, the level of the CSC marker is indicative of the cancer. In other embodiments, the presence of the CSC marker (irrespective of its level) is indicative of the cancer.

The expression ratio of the antigen in in-vivo passaged cells of the tumor: primary cells of the tumor is at least greater than 2:1, 3:1, 4:1, 5:1, 6:1, 7:1, 8:1, 9:1, 10:1, 20:1, 50:1 or even 100:1.

The in-vivo passaged cells of the tumor have preferably been passaged for at least one passage, at least two passages, at least three passages, at least four passages, at least five passages, at least six passages, at least seven passages, at least eight passages, at least nine passages and at least ten passages, at least eleven passages, at least twelve passages, at least thirteen passages, at least fourteen passages, at least fifteen passages, at least sixteen passages, at least seventeen passages, at least eighteen passages, at least nineteen passages, at least twenty passages.

Analyzing the expression of the CSC marker can be performed using methods described herein above.

According to a particular embodiment, the analysis is effected using an antibody which recognizes the CSC marker.

Various types of detectable or reporter moieties may be conjugated to the antibody. These include, but are not limited to, a radioactive isotope (such as $^{[125]}$iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomagraphy (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

Exemplary identifiable moieties include, but are not limited to green fluorescent protein, alkaline phosphatase, peroxidase, histidine tag, biotin, orange fluorescent protein and strepavidin.

It will be appreciated that the identification of CSCs has a variety of applications pertaining to individually optimizing a treatment for cancer, monitoring an-anti cancer treatment in a subject, determining an anti cancer treatment for a subject and identifying an agent capable of treating the cancer.

Thus, according to another aspect of the present invention there is provided a method of monitoring a cancer treatment in a subject, comprising analyzing an amount of an antigen in a primary tumor of the subject following administration of the cancer treatment, wherein a decrease in the level of the antigen as compared to the level of the antigen prior to administration of the cancer treatment is indicative of a therapeutic treatment, wherein the amount of the antigen in in-vivo passaged cells of the tumor: amount of the antigen in primary cells of the tumor is above a predetermined level.

The cancer treatment which is analyzed according to this aspect of the present invention may be an agent or a condition, as further described herein below.

As used herein, the term "agent" refers to a test composition comprising a biological agent or a chemical agent.

Examples of biological agents that may be tested as potential anti cancer agents according to the method of the present invention include, but are not limited to, nucleic acids, e.g., polynucleotides, ribozymes, siRNA and antisense molecules (including without limitation RNA, DNA, RNA/DNA hybrids, peptide nucleic acids, and polynucleotide analogs having altered backbone and/or bass structures or other chemical modifications); proteins, polypeptides (e.g. peptides), carbohydrates, lipids and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

Examples of conditions that may be tested as potential anti cancer agents according to the method of the present invention include, but are not limited to, radiation exposure (such as, gamma radiation, UV radiation, X-radiation).

According to an embodiment of this aspect of the present invention, the "CSC marker" is also assayed prior to contact with the cancer treatment so that a comparison may be made prior to and following treatment.

According to another embodiment of this aspect of the present invention, the agent is subjected to the cancer cells for a period long enough to have an anti cancer effect.

As mentioned, identification of cancer stem cell markers also allows for the treatment of cancers which express such markers.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It will be appreciated, if the cancer stem cell marker is a cell surface antigen, the present inventors contemplate targeting therapeutic moieties to those cells using molecules (e.g. antibodies) which are capable of binding to the markers. The therapeutic moiety can be, for example, a cytotoxic moiety, a toxic moiety, a cytokine moiety and a second antibody moiety comprising a different specificity to the antibodies of the invention.

Preferably, the antibody specifically binds at least one epitope of the CSC marker. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Non-limiting examples of therapeutic moieties which can be conjugated to the antibody of the invention are provided in Table 1, hereinbelow.

TABLE 1

| Nucleic acid sequence | Amino acid sequence | Therapeutic moiety |
|---|---|---|
| EU090068 | ABU63124 | *Pseudomonas* exotoxin |
| AY820132.1 | AAV70486 | Diphtheria toxin |
| A02159 | CAA00227 | interleukin 2 |
| X03884 | P07766 | CD3 |
| NM_000569.6 | NP_000560.5 | CD16 |
| NM_000589.2 | NP_000580.1 | interleukin 4 |
| K02883 | P01892 | HLA-A2 |
| M57627 | P22301 | interleukin 10 |
| EQ975183 | EEF27734 | Ricin toxin |

Table 1.

A therapeutic moiety may also be attached to the antibody of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling of antibodies is provided in details in U.S. Pat. Nos. 3,940,475, 4,289,747, and 4,376,110.

Antibodies which recognize the CSC markers may be attached to particles which comprise cytotoxic agents.

As used herein, the phrase "encapsulating particle" refers to an entity that is characterized by the presence of one or more walls or membranes formulated from lipids and/or fatty acids that form one or more internal voids. The walls or membranes may be concentric or otherwise. The walls or membranes of vesicles may be substantially solid (uniform), or referred to as, for example, liposomes, lipospheres, nanoliposomes, particles, micelles, bubbles, microbubbles, microspheres, nanospheres, nanostructures, microballoons, microcapsules, aerogels, clathrate bound vesicles, hexagonal/cubic/hexagonal II phase structures, and the like.

The lipid component included in the encapsulating particles could include either a lipid derivatized with the targeting molecule, or a lipid having a polar-head chemical group that can be derivatized with the targeting molecule in preformed particles, according to known methods.

Other methods for the covalent attachment of the targeting moiety to the encapsulating particles include the use of an amide, ester, or ether bond, streptavidin and biotin (see, for instance, U.S. Pat. No. 5,171,578), and activation of a polypeptide with carbodiimide followed by coupling to the activated carboxyl groups (U.S. Pat. No. 5,204,096)). Other examples of methods that can be used to covalently bind a polypeptide to a lipid are disclosed in U.S. Pat. No. 5,258,499.

In addition, the present invention contemplates down-regulating an expression of the CSC marker using agents capable of same for the treatment of the cancer.

The down-regulating may be effected on the protein level (e.g. using a neutralizing antibody) or the RNA level (e.g. using an siRNA, a DNAzyme, a ribozyme, miRNA etc.

According to a particular aspect of the present invention the cancer is an atypical teratoid/rhabdoid tumor (ATRT) tumor. Exemplary agents that may be used for the treatment of this cancer are those that target (and down-regulates) at least one of the following polypeptides:semaphorin3C (SEMA3C), lysyl oxidase (LOX), glycoprotein M6A (GPM6A), hepatocyte growth factor (HGF/SF) and aldehyde dehydrogenase1 (ALDH1), thereby treating ATRT.

Thus, an exemplary agent which may be used for the treatment of ATRT is one which targets (and down-regulates) lysyl oxidase (LOX)—e.g. β-Aminopropionitrile (BAPN).

The agent may be administered per se or as part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the component accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Long-term Propagation of a Human Atypical Teratoid Rhabdoid Tumor Xenograft Model as a Platform to Identify, Isolate and Target Cancer Stem Cells Materials and Methods Primary Atypical Teratoid Rhabdoid Tumor sample: The primary ATRT sample was obtained from the patient within 1 hr of surgery. Informed consent was given by the legal guardians of the patient involved according to the declaration of Helsinki.

In vivo xenograft formation: The animal experiments were performed in accordance with the Guidelines for Animal Experiments of Sheba Medical Center. Initial ATRT xenografting to 5-8 weeks old, female, nonobese diabetic immunodeficient (NOD/SCID) mice was performed as previously described (Dekel et al., 2006a). Briefly, primary ATRT tissue was cut into 2-5 mm pieces and implanted subcutaneously in the back of the mouse. Mice were maintained in a pathogen-free environment and monitored weekly for tumor growth. Secondary tumors were detected by palpation every week. Tumors were harvested approximately 1-3 months post implantation or when they reached a size of 1.5 cm diameter. Time to engraftment, time to resection, weight and volume for each engrafted Xn were recorded. Xn tissue was immediately cut into small pieces and processed for further experiments as follows: (i) flash freezing for subsequent molecular characterization of extracted analyses; (ii) formalin fixation and paraffin embedding for future immunohistochemical (IHC) studies; (iii) tissue implantation subcutaneously into the flank of NOD/SCID mice; and (iv) preparation of single cell suspensions as described below for subsequent Xn propagation and in-vitro experiments (in-vitro studies, limiting dilution assays and FACS sorting).

Single cells suspensions were obtained by mincing the samples in Iscove's modification of Dulbecco's medium (IMDM) containing antibiotics (penicillin and streptomycin), followed by treatment with collagenase IV for 2 h at 37° C. Enzymatically treated tissue was triturated using IMDM at twice the volume of the collagenase solution and the suspension filtered (100 μm cell strainer) and washed twice with IMDM containing antibiotics. Erythrocytes were removed by ACK RBS lysis buffer.

Xn serial passages were formed using two methods: 1. Serial injection of approximately $1 \times 10^6$ dissociated cells from freshly retrieved ATRT Xn; Cells were injected in 100 μl 1:1 serum free medium/Matrigel (BD Biosciences, San Jose, Calif.). 2. ATRT Xn tissue was cut into 2-5 mm pieces and implanted subcutaneously in the back of the mouse.

Estimation of the relative frequency of tumor propagating cells: In order to evaluate and compare the tumorigenic activity of Xn cells from low and high passages, serial dilutions ($1 \times 10^6$-50 cells) of cells suspended in 100 μl of PBS and 100 µl Matrigel were injected subcutaneously to the flank of NOD/SCID mice. Estimation of the relative frequency of cancer propagating cells was calculated online using the ELDA software online (bioinfdotwehidotedudotau/software/elda/).

Estimation of the relative frequency of tumor propagating cells in the ALDH high cells: In order to determine the frequency of tumor propagating cells in ALDH high cells respective to ALDH low cells, a limiting dilution assay was used as described above. Briefly, following cell sorting according to ALDHA1 high expression in cells obtained from Xn, sorted populations, [ALDH1$^{hi}$, ALDH1$^{low}$ and unsorted cells (US)] were collected to sterile DMEM. The cells were re-suspended in 100 µl of PBS and 100 µl Matrigel and were injected subcutaneously to the flank of NOD/SCID mice in serial dilutions.

Fluorescence-activated cell sorting (FACS) analysis: FACS analysis of the primary ATRT cells and subsequent fresh Xn derived cells was performed as previously described (Dekel et al., 2006a). Small tumor pieces were dissociated into single cells, washed in RBCs lysis solution (comprised of: 8.3 g NH4Cl, 1.0 g KHCO$_3$, 1.8 ml of 5% EDTA in double distilled H$_2$O) at 1 ml/5 ml cell suspension ratio for 2 min in 4° C. Cells were then filtered through a 30 µm nylon mesh before final centrifugation. All cells were re-suspended in FACS buffer consisting of 0.5% bovine serum albumin (BSA; Sigma-Aldrich, St. Louis) and 0.02% sodium azide in PBS. Surface markers antigens [CD24 (eBiosience, 120247-42), CD34 (Miltenyi, 3008100), CD56 (eBiosience, 1205942), CD90 (Beckman Coulter, IM3600U)] were labeled by incubation with fluorochrome conjugated antibody at a concentration of 5 µg antibody per 10$^6$ cells for 30 min, in the dark, at 4° C. to prevent internalization of antibodies. In addition, 7-amino-actinomycin-D (7AAD; eBioscience, San Diego, Calif.) was used for viable cell gating. All washing steps were performed in FACS buffer. All Quantitative measurements were made in comparison to IgG isotype antibody (eBioscience, San Diego, Calif.). Detection of cells with high ALDH1 enzymatic activity was performed using the ALDEFLUOR kit (StemCell Technologies, Durham, N.C., USA) as previously described (Christophe Ginestier et al., 2007; Dylla et al., 2008). Cells were suspended in Aldefluor assay buffer containing BODIPY-aminoacetaldehyde (BAAA), an uncharged ALDH1 substrate followed by incubation for 30-45 min at 37° C., in the dark. BAAA is taken up only by living cells through passive diffusion and then converted intracellular by ALDH1 into BODIPY-aminoacetate, a negatively charged reaction product, which is retained inside cells expressing high levels of ALDH1, resulting in these cells becoming brightly fluorescent. The fluorescence of these ALDH1 expressing cells (ALDH1+) can be detected by the green fluorescence channel (520-540 nm) of the FACSAria (BD Biosciences, San Jose, Calif.). As a negative control, for each sample of cells an aliquot treated in the same conditions was additionally incubated with diethylaminobenzaldehyde (DEAB), a specific ALDH1 inhibitor. Incubation of cells with the BAAA without the addition of DEAB resulted in a shift in BAAA fluorescence defining the ALDH1+ population. Since only cells with an intact cellular membrane could retain the Aldefluor reaction product, only viable ALDH1+ cells were identified.

FACS sorting: Cells were harvested as described above, filtered through a 30 µm nylon mesh prior to final centrifugation, and then re-suspended either in a FACS buffer or in an ALDEFLUOR buffer. FACS Aria was used in order to enrich for cells expressing surface markers and ALDH1 high activity. A 100-µm nozzle (BD Biosciences, San Jose, Calif.), sheath pressure of 20-25 pounds per square inch (PSI), and an acquisition rate of 1,000-3,000 events per second were used as conditions optimized for ATRT cell sorting. Single viable cells were gated on the basis of 7AAD, and then physically sorted into collection tubes for all subsequent experiments. Data was additionally analyzed and presented using FlowJo software.

Chip Array: The chip array data is deposited in publicly library (GEO). All experiments were performed using Affymetrix HU GENE1.0st oligonucleotide arrays (Pode-Shakked et al., 2009). Total RNA from each sample was used to prepare biotinylated target DNA, according to the manufacturer's recommendations. The target cDNA generated from each sample was processed as per manufacturer's recommendation using an Affymetrix Gene Chip Instrument System. Details of quality control measures can be found online. Significantly changed genes were filtered as changed by at least twofold (p-value: 0.05).

Quantitative Real Time reverse transcription PCR analysis—Gene expression analysis: Quantitative reverse transcription PCR (qRT-PCR) was carried out to determine fold changes in expression of a selection of genes. Total RNA from cells was isolated using an RNeasy Micro Kit (Qiagen GmbH, Hilden, Germany) according to the manufacturer's instructions. cDNA was synthesized using a High Capacity cDNA Reverse Transcription kit (Applied Biosystems, California USA) on total RNA. Real-time PCR was performed using an ABI7900HT sequence detection system (Perkin-Elmer/Applied Biosystems, California, USA) in the presence of TaqMan Gene Expression Master Mix (Applied Biosystems, California, USA). PCR amplification was performed using gene specific TaqMan Gene Expression Assay-Pre-Made kits (Applied Biosystems, California, USA). Each analysis reaction was performed in triplicate. HPRT1 or GAPDH were used as an endogenous control throughout the experimental analyses. PCR results were analyzed using SDS RQ Manager 1.2 software. Statistical analysis was performed using a non-paired 2-tails T-test. Statistical significance was considered at $P<0.05$.

H&E staining: H&E staining of paraffin-embedded tissues: 5 µm sections of paraffin-embedded tissues were mounted on super frost/plus glass and incubated at 60° C. for 40 minutes. After deparaffinization, slides were incubated in Mayer's Hematoxylin solution (Sigma-Aldrich) and incubated with 1% HCl in 70% ethanol for 1 minute. Slides were then incubated for 10 seconds in Eosin (Sigma-Aldrich). Images were produced using Olympus BX51TF.

Immunohistochemical staining of primary ATRT and ATRT Xn: Sections, 4-µm thick, were cut from primary ATRT and ATRT Xn for immunohistochemistry. Immunostainings were performed as previously described (Dekel et al., 2006b). Briefly, the sections were processed to avoid oxidation of antigens. Before immunostaining, sections were treated with 10 mM citrate buffer, PH 6.0 for 10 min at 97° C. for antigen retrieval, followed by 3% H$_2$O$_2$ for 10 min. The slides were subsequently stained using the labeled strepavidin-biotin (LAB-SA) method using a Histostain plus kit (Zymed, San Francisco, Calif. USA). The immunoreaction was visualized by an HRP-based chromogen/substrate system (liquid DAB substrate kit—Zymed, San Francisco, Calif., USA). Anti-human ALDH1 antibody (BD Biosciences, #611195) was used at a dilution of 1:100. The immunoreaction was visualized by an HRP-based chromogen/substrate system (liquid DAB substrate kit—Zymed, San Francisco, Calif., USA). All Sections were also stained for Vimentin, Epithelial Membrane Antigen (EMA), smooth muscle actin (SMA), AE1/AE3, NFP and INI1using conventional immunohistochemical procedures. All antibody dilutions were carried out as recommended by the manufacturers of the staining antibodies.

LOX Activity Assays: The LOX enzyme activity was measured using the Amplex Red fluorescence assay (AAA Bioquest, 15255), as previously described (15843371). The assay reaction mixture consisted of 50 mM sodium borate (pH 8.2), 1.2 M urea, 50 M Amplex Red, 0.1 units/ml horseradish peroxidase, and 10 mM 1,5-diaminopentane (cadaverine) substrate. The protein samples were added to the reaction mix, in the presence or absence of 100 µM BAPN, which was then incubated at 37° C. for 30 minutes. The fluorescent product was measured at 590 nm using an absorbance microplate reader.

MTS—cell viability assay: $5 \times 10^3$ cells were plated in triplicates and grown in 96-well plates over-night. The following day the medium was changed and supplemented with various concentrations of BAPN and the cells were further incubated for 48 h. Cell proliferation was measured using CellTiter 96 Aqueous One Solution Cell Proliferation Assay (Promega) according to the manufacturer's instructions. Briefly, the cells were incubated with the MTS solution for 3 hours at 37° C. and absorbance at 492 nm was determined using a microplate reader. Three independent experiments were carried out.

Cell migration assay: Cells were grown overnight, after which the medium was changed and supplemented with 100 µM BAPN. After 48 hours, a scrape was made through the confluent monolayers with a plastic 1 ml pipette tip. Treated and control cells were then photographed at identical time points (24 and 48 hours).

Statistical analysis: Results are expressed as the mean±S.E.M, unless otherwise indicated. Statistical differences in gene expression between ATRT cell populations were evaluated using the Student's T-test. Statistical differences in the in-vivo experiments were calculated using ANOVE/Chi-square test. For all statistical analysis, the level of significance was set as $p<0.05$ unless otherwise indicated.

Results

Establishment of the MRT Xenograft Model and Cell Culture characterization: A human malignant rhabdoid tumor sample was obtained from a left cervical mass of a newborn male. H&E staining of the primary tumor demonstrated medium to large polygonal tumor cells with round nuclei, fine chromatin and large eosinophilic nucleoli. The morphologic features of the tumor cells, combined with the immunohistochemical profile, confirmed the diagnosis of malignant rhabdoid tumor. Indeed, most tumor cells showed no expression of the INI-1 protein. Flow cytometry analysis was performed on primary tumor cells, demonstrating two cell populations differing in size. For in vitro characterization the cells were grown in two different conditions: DMEM with 10% FBS and serum free medium supplemented with growth factors. Two morphologically distinct types of cells were observed: adherent fibroblast like cells and round cells that were loosely attached to the adherent cells, consistent with the morphology of MRT cells in culture as previously described. Significant cell growth was observed when these cells were cultured in DMEM with 10% FBS. The morphology in culture of primary tumor cells was maintained for about 8 passages. Primary tumor grafts were formed by a subcutaneous transplantation of 2-5 mm tumor pieces into 4 immunodeficient mice (FIG. 6). Tumor engraftment was observed in 4/4 mice allowing further tumor propagation. Sequential propagation of MRT Xn in NOD/SCID mice was performed by tissue samples transplantation or single cell suspensions grafting utilizing a fixed number of $1 \times 10^6$ cells (Table 2 and FIG. 6). Serial propagation allowed us to establish low (<P5), medium (P5-P10) and high-passage (P10-P16) MRT Xn passages that were studied for MRT CSC phenotype characterization and elucidation of pathogenic pathways associated with MRT-initiating capacity (Table 2, herein below and FIG. 6).

TABLE 2

Generation and establishment of human ATRT Xn model in NOD/SCID mice.

| Tissue transplantations | | | Cells Injections* | | | |
| --- | --- | --- | --- | --- | --- | --- |
| (%) engraftment | No. of tissue engrafted | No. of transplantations | (%) engraftment | No. of tumors engrafted | No. of injections | Passage |
| 100 | 4 | 4 | Na | 0 | 0 | P1 |
| 100 | 8 | 8 | 67 | 4 | 6 | P2 |
| 93 | 13 | 14 | 83 | 10 | 12 | P3 |
| 100 | 6 | 6 | 88 | 7 | 8 | P4 |
| 75 | 3 | 4 | 100 | 8 | 8 | P5 |
| 67 | 4 | 6 | 100 | 4 | 4 | P6 |
| 50 | 2 | 4 | 100 | 2 | 2 | P7 |
| 50 | 1 | 2 | 50 | 2 | 4 | P8 |
| na | 0 | 0 | 100 | 4 | 4 | P9 |
| na | 0 | 0 | 100 | 2 | 2 | P10 |
| 100 | 2 | 2 | 100 | 4 | 4 | P11 |
| 100 | 2 | 2 | 100 | 2 | 2 | P12 |
| 100 | 2 | 2 | 100 | 4 | 4 | P13 |
| 100 | 2 | 2 | 100 | 4 | 4 | P14 |
| 100 | 1 | 1 | 100 | 4 | 4 | P15 |
| na | 0 | 0 | 100 | 4 | 4 | P16 |
| 88 | 50 | 57 | 90 | 65 | 72 | Total |

Generation of primary human ATRT Xn from serial $1 \times 10^{6*}$ cell injections and tissue transplantations. Primary tumor tissue was obtained from ATRT of a newborn infant.

Long-Term Propagation of MRT is Associated with an Increased CSC Frequency

Sequential propagation of MRT Xn with a fixed cell number of $1 \times 10^6$ cells correlated with shorter time to tumor engraftment and accelerated tumor growth (FIG. 1A and Table 3) indicating the promotion of tumor aggressiveness along passages.

TABLE 3

ATRT Xn frequency and characteristics during propagation

| Xn weight/days to resection ratio (mean) | Days to engraftment (mean) | Engraftment rate (%) | Passage | |
| --- | --- | --- | --- | --- |
| 0.04 | 34 | 4/6 | P2 | Low |
| 0.07 | 23 | 10/12 | P3 | |
| 0.08 | 24 | 7/8 | P4 | |
| 0.06 | 26 | 21/26 (80) | | |
| 0.11 | 15 | 8/8 | P5 | Intermediate |
| 0.09 | 22 | 4/4 | P6 | |
| 0.12 | 15 | 2/2 | P7 | |
| 0.10 | 28 | 2/4 | P8 | |
| 0.06 | 23 | 4/4 | P9 | |
| 0.06 | 22 | 2/2 | P10 | |
| 0.09 | 20 | 22/24 (92) | | |
| 0.05 | 19 | 4/4 | P11 | High |
| 0.12 | 20 | 2/2 | P12 | |
| 0.08 | 16 | 4/4 | P13 | |
| 0.11 | 16 | 4/4 | P14 | |
| 0.19 | 14 | 4/4 | P15 | |
| 0.16 | 14 | 4/4 | P16 | |
| 0.12 | 16 | 22/22 (100) | | |

Table summarizing the frequency and characteristics of secondary tumor formation from 1×10⁶ cells obtained from ATRT Xn and further propagated. During serial propagation of ATRT Xn shorter time to tumor engraftment and accelerated tumor growth were noticed. In the comparison between low and intermediate Xn passages *p<0.01.

The present inventors next queried whether CSC capacity is functionally enhanced with MRT propagation. They performed limiting dilution xenotransplantation experiments with MRT cells derived from low, intermediate and high-passage Xn. This analysis shows significant positive selection for CSC frequency in high-passage Xn (Table 4).

TABLE 4 limiting dilution xenotransplantation summary representing tumor CSC frequency during propagation.

| Number of grafted tumors/ number of injections | | | Number of Injected |
| --- | --- | --- | --- |
| High | Intermediate | Low | Tumor Cells |
| 9/10 | 4/6 | 1/10 | 1000 |
| 2/2 | 1/2 | — | 750 |
| 3/5 | 2/3 | 2/10 | 500 |
| 2/2 | — | — | 250 |
| 6/8 | — | 1/16 | 100 |
| 1/2 | — | 0/4 | 50 |
| 1/120 | 1/1801 | 1/3930 | Tumor propagating cell frequency (95% CI) |

Having observed that high-passage MRT Xn enriches for higher numbers of CSCs, the histological and immunohistochemical changes that accompany the acquisition of the CSC phenotype along passages were analyzed (FIGS. 1B-C). H&E staining revealed that Xn derived tumors maintain the basic Rhabdoid-like cellular morphology. Nevertheless, some morphological differences were observed in high generation Xn including the acquisition of spindle like cell morphology, vast areas of necrosis, less apoptotic bodies and more mitoses (FIG. 1B). Immunohistochemistry (IHC) staining disclosed both primary tumor and Xn tissues to strongly express the mesenchymal marker vimentin (FIG. 1C). However, in contrast to the primary tumor, high generation Xn showed loss of differentiation markers including epithelial membrane antigen (EMA), cytokeratin AE1/AE3 and neurofilament protein (NFP) (FIG. 1C). In order to validate the IHC results, qRT-PCR was performed on primary tumor, early and late Xn. The gene expression analysis demonstrated the maintenance of vimentin alongside the loss of the epithelial differentiation marker, E-cadherin (FIG. 1D). Thus, enhanced CSC frequency was associated with MRT Xn that retains similar histopathologic rhabdoid features and show de-differentiation towards a mesenchymal phenotype.

Figure 2A:
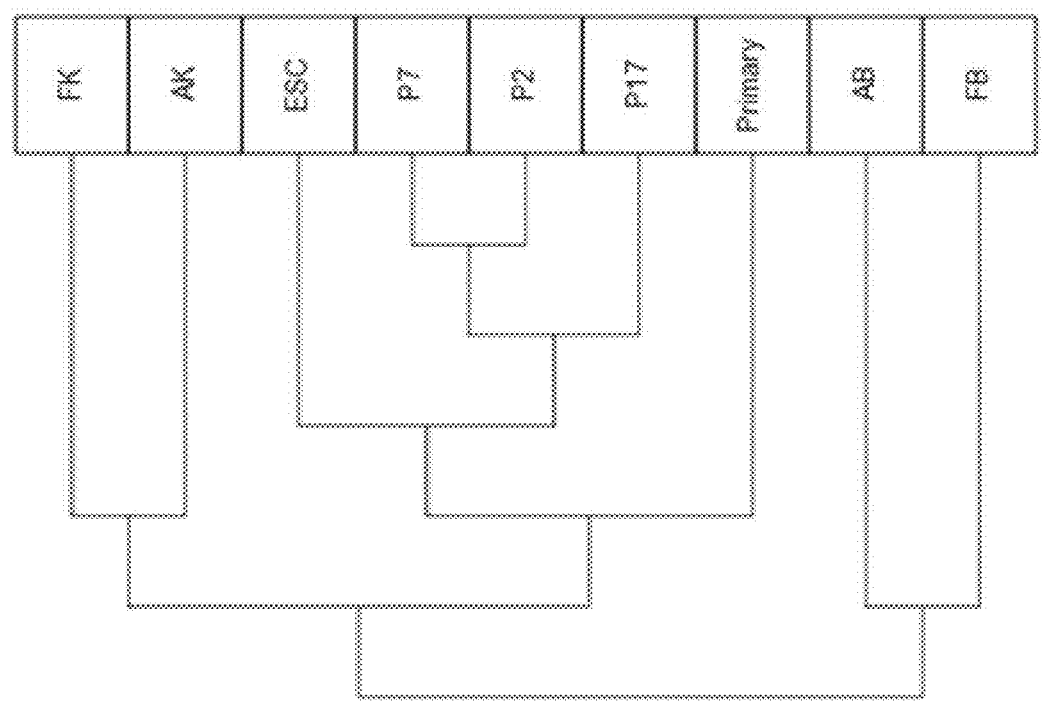
Figure 2B:
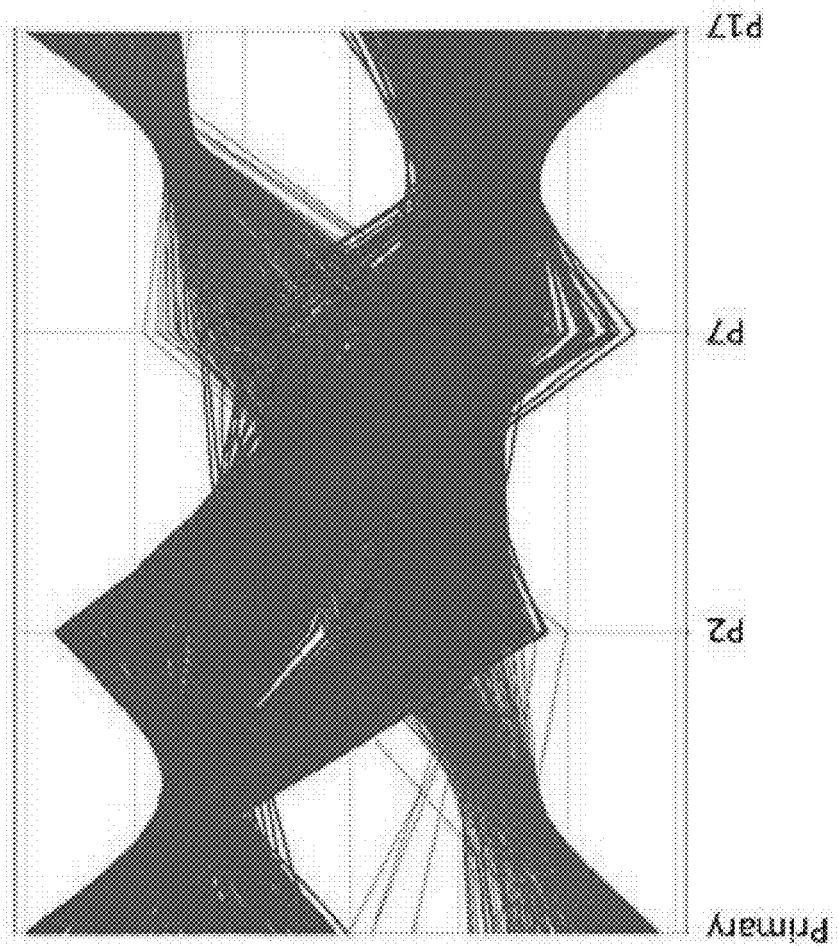

Global Gene Signature Associated with Enhanced Tumor Initiating Activity Reveals Putative CSC Biomarkers The present inventors next sought to characterize the global molecular profile of sequential MRT Xn accompanying the selection for the CSC phenotype. For this purpose, they performed a microarray gene expression analysis comparing several different samples: 1. primary MRT, 2. Early MRT Xn (P2), 3. Intermediate MRT Xn (P7), 4. Late MRT Xn (P16), 5. Human embryonic stem cells (hESCs), 6. Fetal kidney (FK), 7. Adult kidney (AK), 8. Fetal brain (FB), 9. Adult brain (AB). Global expression analysis showed that propagated MRT Xn cells clustered more closely with hESCs rather than with their primary tumor of origin as illustrated by hierarchical clustering (FIG. 2A). In addition there was a greater similarity of the Xn tissues with human fetal tissues. Altogether, these results confirm the selection for stem cell phenotype during tumor propagation. Closer examination of primary MRT and sequential MRT Xn (low, intermediate and high-passage) identified a variety of gene expression patterns including two major clusters of genes that were up-regulated and down-regulated through-out the passages (FIG. 2B). The cohort of up-regulated genes included molecules that accompany the acquisition of the observed CSC phenotype such as semaphorin3C (SEMA3C), lysyl oxidase (LOX), glycoprotein M6A (GPM6A), hepatocyte growth factor (HGF/SF) and aldehyde dehydrogenase1 (ALDH1) (FIG. 2C). This gene expression profile could also verify tumor biology along passages as manifested by gene heat map revealing later passages as highly proliferative (e.g. K1-67, CDK1 and AURKA) (FIG. 2D). In addition, ingenuity© function analysis demonstrated decreased necrosis, cell death and differentiation of cells (FIG. 2E), both supporting the results obtained from the H&E and IHC staining that demonstrated decreased apoptosis, increased mitoses and loss of differentiation markers in high passages Xn compared to primary tumor and low passages Xn. Thus, the sequential Xn propagation model generated putative biomarker molecules involved in continued tumor initiation and progression and the gain of CSC phenotype in MRT.

Functional Validation of ALDH1 as MRT CSC Biomarker

Figure 3A:
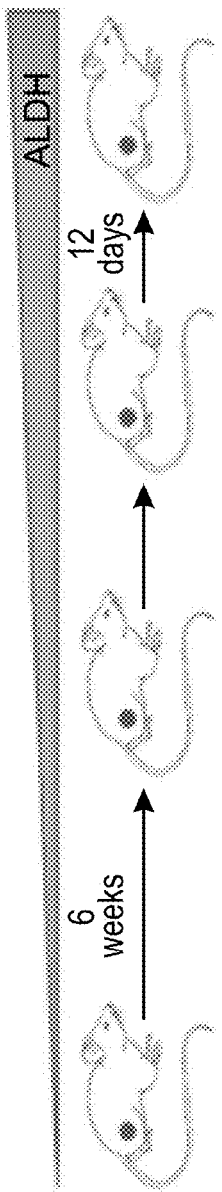
Figure 3B:
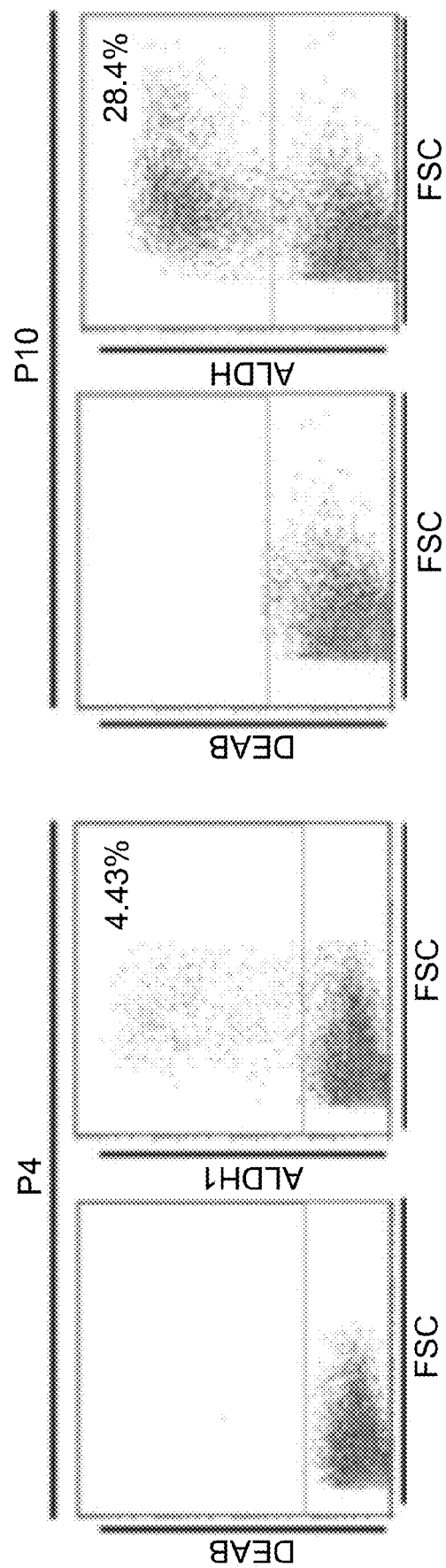
Figure 3C:
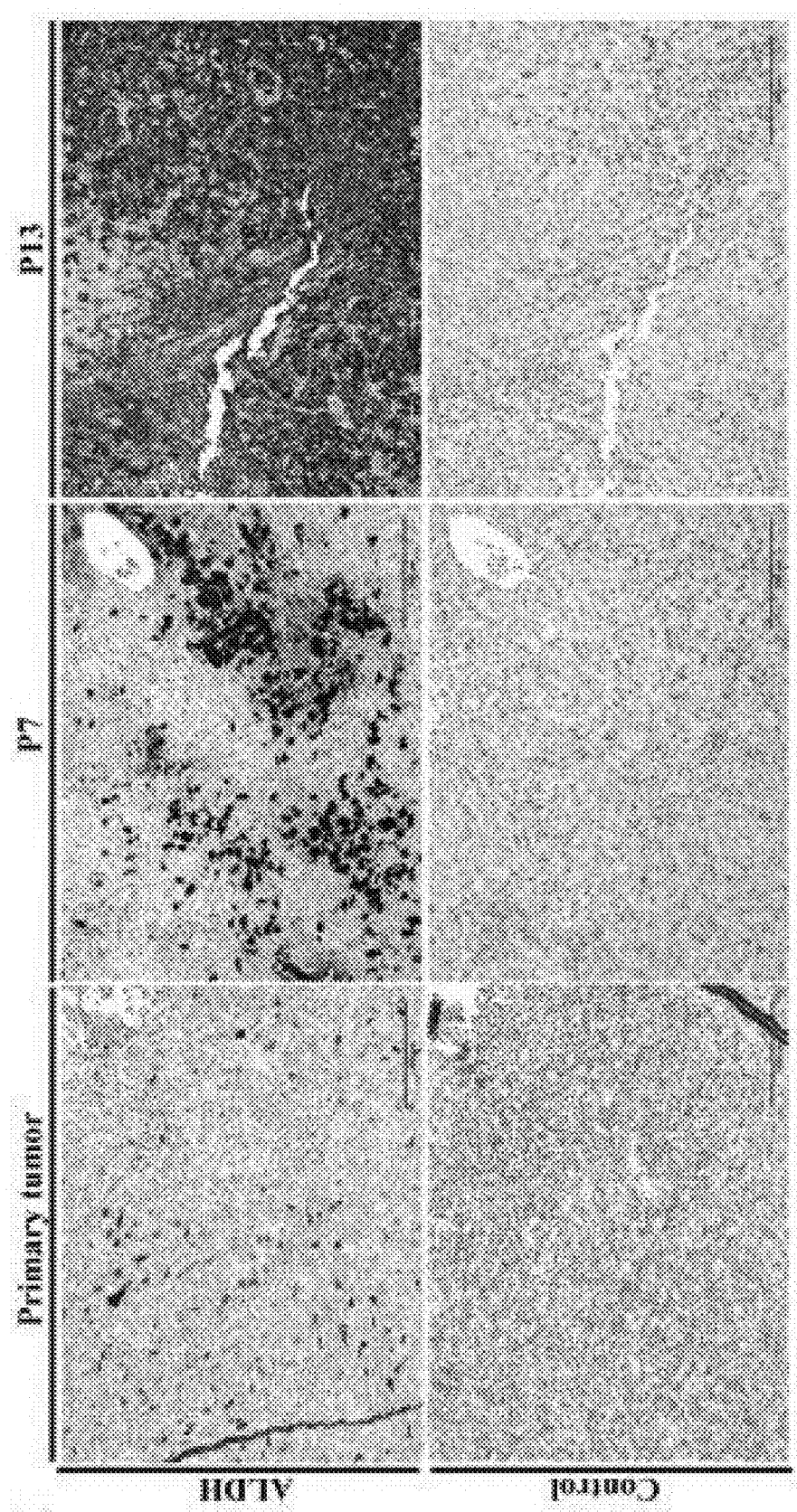
Figure 3E:
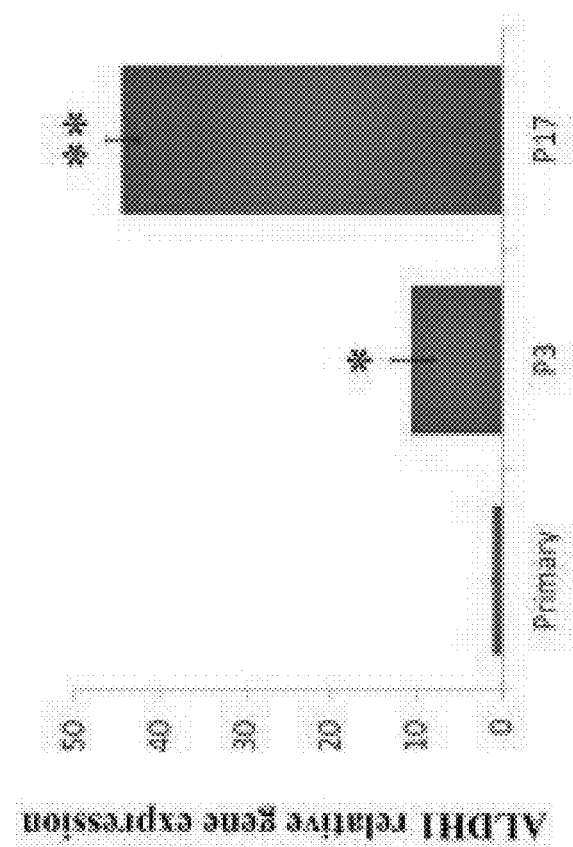
Figure 3D:
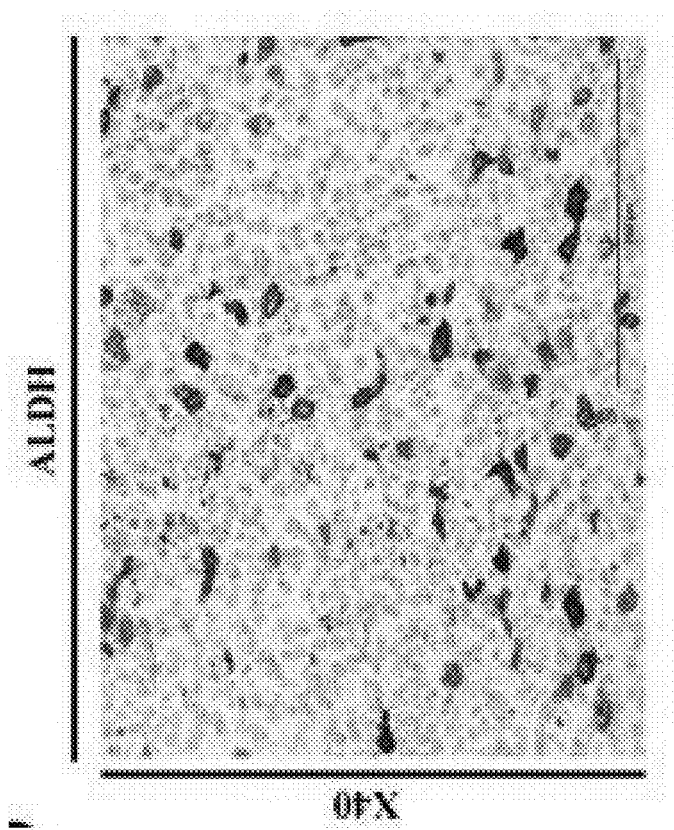
Figure 4A:
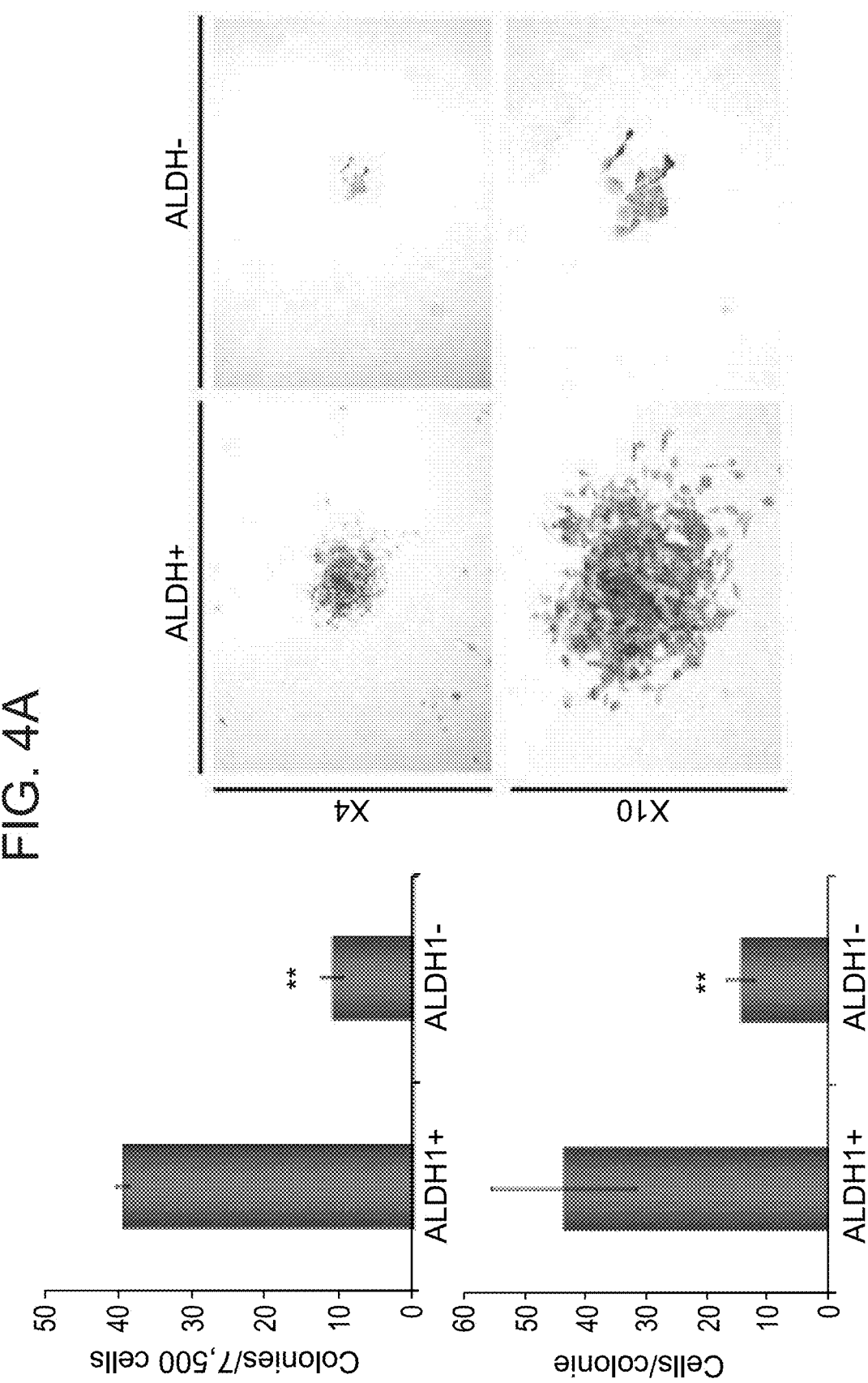

Having observed that the presently disclosed molecular screen independently pinpointed ALDH1 as a marker of CSC phenotype gain in MRT the present inventors further examined its expression and functional roles. Importantly, ALDH1 has been suggested as a CSC marker, and could therefore validate the approach. Expression analysis demonstrated that the proportion of ALDH1 significantly increased along tumor propagation (FIG. 3A). FACS analysis to quantify the proportion of ALDH1 population in the different stages of Xn propagation revealed that in low passage Xn cells (passage 4), only 4% of cells were ALDH1+ in comparison to 25% of cells in late passage (passage 10) (FIG. 3B). In addition, ALDH1 IHC staining demonstrated the increased expression of ALDH1 along the passages (FIG. 3C). Furthermore, the ALDH1$^{high}$ expressing cells were mainly the large rhabdoid cells (FIG. 3D). At the gene expression level, qRT-PCR analysis revealed high ALDH1 expression in late passages, about 40 times higher in comparison to primary tumor (FIG. 3E). The present inventors then sorted the ALDH1+ fraction so as to determine whether they qualify as CSCs. A defining property of cancer stem cells is their functional ability to form clones in-vitro. Colony forming assays showed significantly higher number of clones and larger colonies in ALDH1+ compared to ALDH1-MRT cells in accordance with the CSC phenotype (FIG. 4A). In addition, CSCs are defined by their ability to reform tumors upon transplantation into immunodeficient mice. To investigate the tumorigenicity of ALDH1+ cells in vivo, decreasing amounts of FACS purified ALDH1+ and ALDH1− cells were injected in the flanks of NOD/SCID mice using the limiting dilution analysis (18). Unsorted cells were injected as control (Table 2). In the low passage (P3) 4 out of 6 mice injected with 2000 or less ALDH1+ cells formed tumors compared to none of the mice injected with ALDH1− cells (p<0.05). In high passage (P12) all the mice injected with 1000 or less ALDH1+ cells formed secondary tumors while only 2 out of 11 of the mice injected with ALDH1− cells developed a tumor (p<0.001), suggesting that this population was relatively depleted of tumor initiating cells (Table 2). Importantly, tumors that arose from ALDH1+ cells could be further serially transplanted into secondary recipients, consistent with the presence of tumor initiation capacity in this population, demonstrating in-vivo self-renewal capacity of ALDH+ cells (FIG. 4B). Altogether, these data show that ALDH1 is marker for MRT CSC validating the link of CSC phenotype gain we defined with long-term propagation to specific molecules such as ALDH1. In order to better characterize sorted ALDH+ CSCs at the molecular level and determine whether they enrich for the CSC biomarkers predicted by long-term propagation, an RNA sequencing experiment on sorted ALDH+ and ALDH− cells obtained from MRT Xn was performed (FIG. 4C). Interestingly, it was found that among the most up-regulated genes in the ALDH+ cells in comparison to ALDH− cells were those significantly overexpressed genes in late Xn passages in comparison to the primary tumor (e.g. ANXA1, GPM6A, HGF and LOX) (FIG. 4C). qRT-PCR analysis was performed, validating high LOX expression in ALDH+ in comparison to ALDH− cells (FIG. 4D). These results emphasize the validity of our Xn propagation technique as a model to identify molecules and pathways linked with tumor aggressiveness and CSC frequency. The high expression of LOX in progressive MRT Xn and in the sorted ALDH+ CSC fraction led us to examine whether LOX can serve as a therapeutic target.

Functional Validation of LOX Inhibitor as MRT CSC Therapeutic Agent.

Figure 5B:
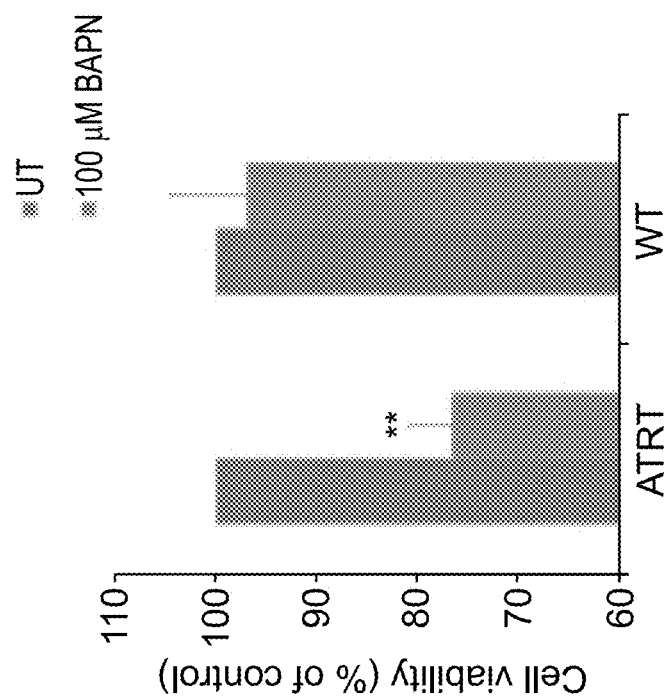
Figure 5A:
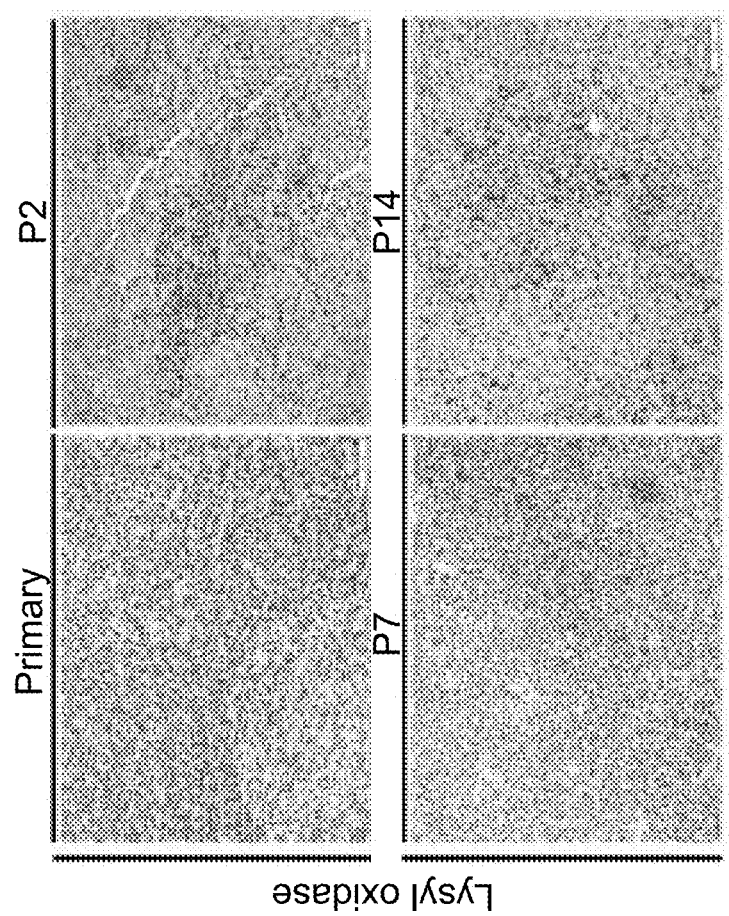
Figure 7A:
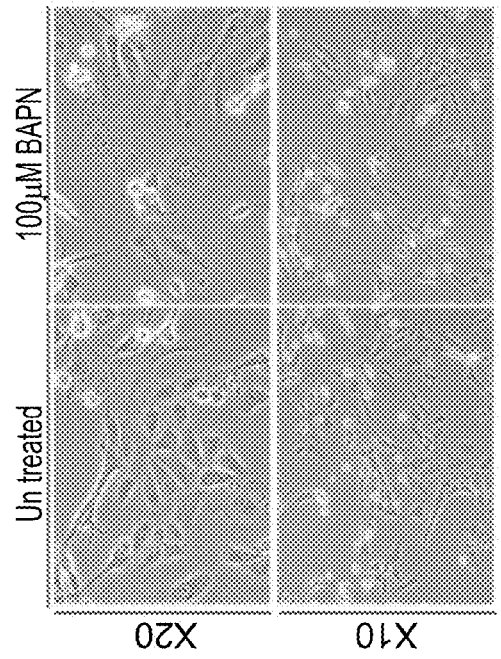
Figure 7B:
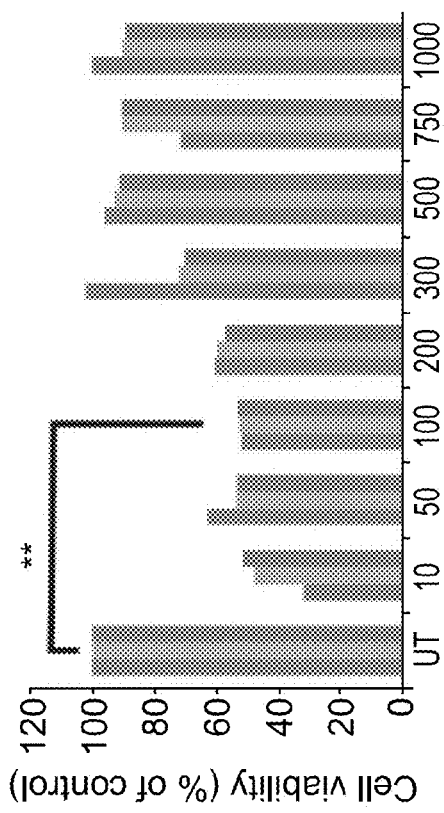
Figure 7D:
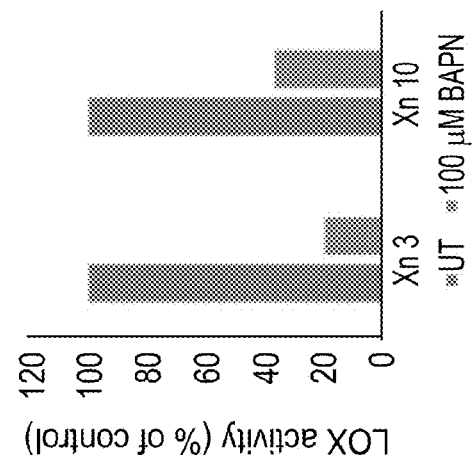
Figure 7C:
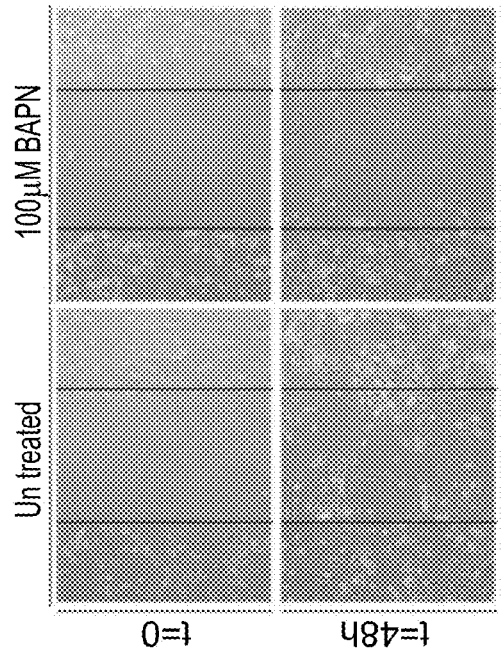

LOX, an extracellular matrix-remodeling enzyme regulates events such as chromatin compaction (19), gene transcription (20, 21), as well as early cell differentiation and tissue development (22), and therefore relevant to MRT which is characterized by INI-1 loss that regulates similar activities. Recent studies have shown that LOX is overexpressed in several malignancies, including breast, colon and pancreatic tumors (23, 24) and is associated with tumor progression and metastases (25). IHC staining analyzing the expression of LOX in primary MRT, early (P2), intermediate (P7) and late (P14) Xn passages confirmed a wide increasing expression throughout the passages with a significant expression in the rhabdoid cells (FIG. 5A). Previously, BAPN, a LOX inhibitor, was shown to have positive effects on various cancer cells. (23). Since the LOX gene was up-regulated in Xn during propagation and CSC phenotype selection as well as in sorted MRT CSCs, the present inventors sought to examine whether LOX inhibition has an effect on MRT cells. First, Xn cells were grown in different concentration of BAPN for 48 h. An MTS analysis, examining cell viability, demonstrated significantly reduced proliferation following treatment with 100 µM BAPN in three different experiments (data not shown). Next, they examined the effect of BAPN on WT Xn cells, a common pediatric solid tumor of the kidney that was serially propagated in mice. The results demonstrated no effect on WT cell proliferation, indicating a specific effect of LOX inhibition on MRT cells (FIG. 5B). The present inventors next examined the morphology of MRT cells as a result of BAPN treatment and showed that the treatment induced morphological changes, including nuclear condensation and cell swallowing (FIG. 5C). Importantly, a migration assay revealed that BAPN treatment for 48 h significant inhibited MRT cell migration capacity, as compared to un-treated cells (FIG. 5D). Since all the in-vitro results were obtained using an intermediate Xn passage (P10), the present inventors set to determine whether BAPN will have a similar effect on cells more similar to the primary tumor. Similar experiments were conducted on P2 cells and revealed the same results (FIGS. 7A-C). LOX activity measurement validated that 100 µM BAPN indeed significantly inhibited LOX activity (FIG. 7D). These results suggest that targeting a novel MRT CSC biomarker can abrogate tumor growth and warrants LOX as a possible MRT therapeutic target.

References For Example 1

1. Pode-Shakked N, Metsuyanim S, Rom-Gross E, Mor Y, Fridman E, Goldstein I, et al. Developmental tumourigenesis: NCAM as a putative marker for the malignant renal stem/progenitor cell population. Journal of cellular and molecular medicine. 2009 August; 13(8B): 1792-808.
2. Dekel B, Metsuyanim S, Schmidt-Ott K M, Fridman E, Jacob-Hirsch J, Simon A, et al. Multiple imprinted and stemness genes provide a link between normal and tumor progenitor cells of the developing human kidney. Cancer research. 2006 Jun. 15; 66(12):6040-9.
3. Metsuyanim S, Pode-Shakked N, Schmidt-Ott K M, Keshet G, Rechavi G, Blumental D, et al. Accumulation of malignant renal stem cells is associated with epigenetic changes in normal renal progenitor genes. Stem cells (Dayton, Ohio). 2008 July; 26(7):1808-17.
4. Pode-Shakked N, Dekel B. Wilms tumor-a renal stem cell malignancy? Pediatric nephrology (Berlin, Germany) 2011 September; 26(9):1535-43.
5. Pode-Shakked N, Shukrun R, Mark-Danieli M, Tsvetkov P, Bahar S, Pri-Chen S, et al. The isolation and characterization of renal cancer initiating cells from human Wilms' tumour xenografts unveils new therapeutic targets. EMBO molecular medicine. 2013 January; 5(1):18-37.
6. Shukrun R, Dekel B, Pode-Shakked N, Pleniceanu O, Omer D, Vax E, et al. Wilms' Tumor Blastemal Stem Cells Dedifferentiate to Propagate the Tumor Bulk. Stem Cell Reports. 2014.
7. Parham D M, Weeks D A, Beckwith J B. The clinicopathologic spectrum of putative extrarenal rhabdoid tumors. An analysis of 42 cases studied with immunohistochemistry or electron microscopy. The American journal of surgical pathology. 1994 October; 18(10):1010-29.
8. Wick M R, Ritter J H, Dehner L P. Malignant rhabdoid tumors: a clinicopathologic review and conceptual discussion. Seminars in diagnostic pathology. 1995 August; 12(3):233-48.
9. Versteege I, Sevenet N, Lange J, Rousseau-Merck M F, Ambros P, Handgretinger R, et al. Truncating mutations of hSNF5/INI1 in aggressive paediatric cancer. Nature. 1998 Jul. 9; 394(6689):203-6.
10. Olson T A, Bayar E, Kosnik E, Hamoudi A B, Klopfenstein K J, Pieters R S, et al. Successful treatment of disseminated central nervous system malignant rhabdoid tumor. Journal of pediatric hematology/oncology. 1995 February; 17(1):71-5.
11. Douglass E C, Valentine M, Rowe S T, Parham D M, Wilimas J A, Sanders J M, et al. Malignant rhabdoid tumor: a highly malignant childhood tumor with minimal karyotypic changes. Genes, chromosomes & cancer. 1990 September; 2(3):210-6.
12. Rorke L B, Packer R J, Biegel J A. Central nervous system atypical teratoid/rhabdoid tumors of infancy and childhood: definition of an entity. Journal of neurosurgery. 1996 July; 85(1): 56-65.
13. Biegel J A, Tan L, Zhang F, Wainwright L, Russo P, Rorke L B. Alterations of the hSNF5INI1 gene in central nervous system atypical teratoid/rhabdoid tumors and renal and extrarenal rhabdoid tumors. Clin Cancer Res. 2002 November; 8(11):3461-7.
14. Biegel J A, Zhou J Y, Rorke L B, Stenstrom C, Wainwright L M, Fogelgren B. Germ-line and acquired mutations of INI1 in atypical teratoid and rhabdoid tumors. Cancer research. 1999 Jan. 1; 59(1):74-9.
15. Euskirchen G, Auerbach R K, Snyder M. SWI/SNF chromatin-remodeling factors: multiscale analyses and diverse functions. The Journal of biological chemistry. 2012 Sep. 7; 287(37):30897-905.
16. Tomlinson G E, Breslow N E, Dome J, Guthrie K A, Norkool P, Li S, et al. Rhabdoid tumor of the kidney in the National Wilms' Tumor Study: age at diagnosis as a prognostic factor. J Clin Oncol. 2005 Oct. 20; 23(30):7641-5.
17. Ginestier C, Hur M H, Charafe-Jauffret E, Monville F, Dutcher J, Brown M, et al. ALDH1 is a marker of normal and malignant human mammary stem cells and a predictor of poor clinical outcome. Cell stem cell. 2007 November; 1(5):555-67.
18. Hu Y, Smyth G K. ELDA: extreme limiting dilution analysis for comparing depleted and enriched populations in stem cell and other assays. Journal of immunological methods. 2009 Aug. 15; 347(1-2):70-8.
19. Mello M L, Contente S, Vidal B C, Planding W, Schenck U. Modulation of ras transformation affecting chromatin supraorganization as assessed by image analysis. Experimental cell research. 1995 October; 220(2):374-82.
20. Di Donato A, Lacal J C, Di Duca M, Giampuzzi M, Ghiggeri G, Gusmano R. Micro-injection of recombinant lysyl oxidase blocks oncogenic p21-Ha-Ras and progesterone effects on *Xenopus laevis* oocyte maturation. FEBS letters. 1997 Dec. 8; 419(1):63-8.
21. Giampuzzi M, Botti G, Di Duca M, Arata L, Ghiggeri G, Gusmano R, et al. Lysyl oxidase activates the transcription activity of human collagene III promoter. Possible involvement of Ku antigen. The Journal of biological chemistry. 2000 Nov. 17; 275(46):36341-9.
22. Maki J M, Rasanen J, Tikkanen H, Sormunen R, Makikallio K, Kivirikko K I, et al. Inactivation of the lysyl oxidase gene Lox leads to aortic aneurysms, cardiovascular dysfunction, and perinatal death in mice. Circulation. 2002 Nov. 5; 106(19):2503-9.
23. Bondareva A, Downey C M, Ayres F, Liu W, Boyd S K, Hallgrimsson B, et al. The lysyl oxidase inhibitor, beta-aminopropionitrile, diminishes the metastatic colonization potential of circulating breast cancer cells. PloS one. 2009; 4(5):e5620.
24. Melstrom L G, Bentrem D J, Salabat M R, Kennedy T J, Ding X Z, Strouch M, et al. Overexpression of 5-lipoxygenase in colon polyps and cancer and the effect of 5-LOX inhibitors in vitro and in a murine model. Clin Cancer Res. 2008 Oct. 15; 14(20):6525-30.
25. Barker H E, Cox T R, Erler J T. The rationale for targeting the LOX family in cancer. Nature reviews. 2012 August; 12(8):540-52.
26. Findlay V J, Wang C, Watson D K, Camp E R. Epithelial-to-mesenchymal transition and the cancer stem cell phenotype: insights from cancer biology with therapeutic implications for colorectal cancer. Cancer gene therapy. 2014 May 2.
27. Marjanovic N D, Weinberg R A, Chaffer C L. Poised with purpose: cell plasticity enhances tumorigenicity. Cell cycle (Georgetown, Tex. 2013 Sep. 1; 12(17):2713-4.
28. Lander A D. The 'stem cell' concept: is it holding us back? Journal of biology. 2009; 8(8):70.
29. Bertucci F, Bouvier-Labit C, Finetti P, Metellus P, Adelaide J, Mokhtari K, et al. Gene expression profiling of solitary fibrous tumors. PloS one. 2013; 8(5):e64497.
30. Ma L J, Li Y G, Huang L, Han M, Ma B J, Sun B J, et al. [Expression of LOX and MMP-2 in gastric cancer tissue and the effects of LOX and MMP-2 on tumor invasion and metastasis]. Zhonghua zhong liu za zhi [Chinese journal of oncology]. 2011 January; 33(1):37-41.
31. Thomas C, Karnoub A E. Lysyl oxidase at the crossroads of mesenchymal stem cells and epithelial-mesenchymal transition. Oncotarget. 2013 March; 4(3):376-7.
32. Kordes U, Gesk S, Fruhwald M C, Graf N, Leuschner I, Hasselblatt M, et al. Clinical and molecular features in patients with atypical teratoid rhabdoid tumor or malignant rhabdoid tumor. Genes, chromosomes & cancer. 2003 February; 49(2):176-81.

Example 2

Long-term Propagation of Human Wilm's Tumor and Ewing Sarcoma Xenograft

Materials and Methods

In vivo xenograft formation and time to engraftment calculation: The animal experiments were performed in accordance with the Guidelines for Animal Experiments of Sheba Medical Center. Initial Tumor xenografting to 5-8 weeks old, female, nonobese diabetic immunodeficient (NOD/SCID) mice was performed as described herein above. Briefly, primary Tumor tissue was cut into 2-5 mm pieces and implanted subcutaneously in the back of the mouse. Mice were maintained in a pathogen-free environment and monitored weekly for tumor growth. Secondary tumors were detected by palpation every week. Tumors were harvested when they reached a size of 1.5 cm diameter. Time to engraftment, time to resection, weight and volume for each engrafted Xn were recorded. Xn tissue was immediately cut into small pieces and processed for tissue implantation subcutaneously into the flank of NOD/SCID mice and preparation of single cell suspensions as described below for subsequent Xn propagation. Single cells suspensions were obtained by mincing the samples in Iscove's modification of Dulbecco's medium (IMDM) containing antibiotics (penicillin and streptomycin), followed by treatment with collagenase IV for 2 h at 37° C. Enzymatically treated tissue was triturated using IMDM at twice the volume of the collagenase solution and the suspension filtered (100 µm cell strainer) and washed twice with IMDM containing antibiotics. Erythrocytes were removed by ACK RBS lysis buffer.

Xn serial passages were formed in two methods: 1.Serial injection of approximately $1 \times 10^6$ dissociated cells from freshly retrieved Xn; Cells were injected in 100 µl 1:1 serum free medium/Matrigel (BD Biosciences, San Jose, Calif.). 2. Xn tissue was cut into 2-5 mm pieces and implanted subcutaneously in the back of the mouse.

Results

Sequential propagation of Ewing sarcoma (FIG. 8A) and Wilm's tumor (FIG. 8B) Xn correlated with shorter time to tumor engraftment, indicating changes in tumor behavior towards more aggressive phenotype.

Example 3

Long-term Propagation of Human Pleuropulmonary Blastoma (PPB) Xenograft

Materials and Methods

In vivo xenograft formation and time to engraftment calculation: The animal experiments were performed in accordance with the Guidelines for Animal Experiments of Sheba Medical Center. Initial Tumor xenografting to 5-8 weeks old, female, nonobese diabetic immunodeficient (NOD/SCID) mice was performed as described herein above. Briefly, primary Tumor tissue was cut into 2-5 mm pieces and implanted subcutaneously in the back of the mouse. Mice were maintained in a pathogen-free environment and monitored weekly for tumor growth. Secondary tumors were detected by palpation every week. Tumors were harvested when they reached a size of 1.5 cm diameter. Time to engraftment, time to resection, weight and volume for each engrafted Xn were recorded. Xn tissue was immediately cut into small pieces and processed for tissue implantation subcutaneously into the flank of NOD/SCID mice and preparation of single cell suspensions as described below for subsequent Xn propagation. Single cells suspensions were obtained by mincing the samples in Iscove's modification of Dulbecco's medium (IMDM) containing antibiotics (penicillin and streptomycin), followed by treatment with collagenase IV for 2 h at 37° C. Enzymatically treated tissue was triturated using IMDM at twice the volume of the collagenase solution and the suspension filtered (100 µm cell strainer) and washed twice with IMDM containing antibiotics. Erythrocytes were removed by ACK RBS lysis buffer.

Xn serial passages were formed in two methods: 1.Serial injection of approximately $1 \times 10^6$ dissociated cells from freshly retrieved Xn; Cells were injected in 100 µl 1:1 serum free medium/Matrigel (BD Biosciences, San Jose, Calif.). 2. Xn tissue was cut into 2-5 mm pieces and implanted subcutaneously in the back of the mouse.

Estimation of the relative frequency of tumor propagating cells: In order to evaluate and compare the tumorigenic activity of Xn cells from low and high passages, serial dilutions ($1 \times 10^6$-50 cells) of cells suspended in 100 µl of PBS and 100 µl Matrigel were injected subcutaneously to the flank of NOD/SCID mice. Estimation of the relative frequency of cancer propagating cells was calculated online using the ELDA software online (bioinfdotwehidotedudotau/software/elda/).

Chip Array: All experiments were performed using Affymetrix HU GENE1.0st oligonucleotide arrays. Total RNA from each sample was used to prepare biotinylated target cDNA, according to the manufacturer's recommendations. The target cDNA generated from each sample was processed as per manufacturer's recommendation using an Affymetrix Gene Chip Instrument System. Details of quality control measures can be found online. Significantly changed genes were filtered as changed by at least twofold (p-value: 0.05).

Immunohistochemical staining of PPB Xn. Sections, 4-µm thick, were cut from primary PPB and PPB Xn for immunohistochemistry. Immunostainings were performed as described herein above. Briefly, the sections were processed to avoid oxidation of antigens. Before immunostaining, sections were treated with 10 mM citrate buffer, PH 6.0 for 10 min at 97° C. for antigen retrieval, followed by 3% $H_2O_2$ for 10 min. The slides were subsequently stained using the labeled strepavidin-biotin (LAB-SA) method using a Histostain plus kit (Zymed, San Francisco, Calif., USA). The immunoreaction was visualized by an HRP-based chromogen/substrate system (liquid DAB substrate kit—Zymed, San Francisco, Calif., USA). Anti-human NCAM antibody (BD Biosciences, #611195) was used at a dilution of 1:1200. The immunoreaction was visualized by an HRP-based chromogen/substrate system (liquid DAB substrate kit—Zymed, San Francisco, Calif., USA).

Quantitative Real Time reverse transcription PCR analysis—Gene expression analysis: Quantitative reverse transcription PCR (qRT-PCR) was carried out to determine fold changes in expression of NCAM. Total RNA from cells was isolated using an RNeasy Micro Kit (Qiagen GmbH, Hilden, Germany) according to the manufacturer's instructions. cDNA was synthesized using a High Capacity cDNA Reverse Transcription kit (Applied Biosystems, California USA) on total RNA. Real-time PCR was performed using an ABI7900HT sequence detection system (Perkin-Elmer/Applied Biosystems, California, USA) in the presence of TaqMan Gene Expression Master Mix (Applied Biosystems, California, USA). PCR amplification was performed using gene specific TaqMan Gene Expression Assay-Pre-Made kits (Applied Biosystems, California, USA). Each analysis reaction was performed in triplicate. HPRT1 or GAPDH were used as an endogenous control throughout the experimental analyses. PCR results were analyzed using SDS RQ Manager 1.2 software. Statistical analysis was performed using a non-paired 2-tails T-test. Statistical significance was considered at $P<0.05$.

Results

Sequential propagation of PPB Xn correlated with shorter time to tumor engraftment and accelerated tumor growth indicating the promotion of tumor aggressiveness along passages. In comparison between early (passages 1-4) and late Xn (passages 7-12) passage time to tumor engraftment declined from 58 to 33 days (p<0.02), as shown in Table 6 herein below.

TABLE 6

| | Engraftment rate (%) | Time to engraftment (Days)* | Time to resection (Days) | Average weight | Average Volume | Weight/time to resection ratio(mean) |
|---|---|---|---|---|---|---|
| Early | 63.16 | 58.08 | 77.57 | 1.43 | 0.88 | 0.02 |
| Late | 87.50 | 33.85 | 51.94 | 1.83 | 1.03 | 0.04 |

Limiting dilution xenotransplantation experiments were performed with PPB cells derived from early and late-passage Xn. This analysis shows significant positive selection for CSC frequency in high-passage Xn. In comparison between early and late Xn passages CSC frequency elevated from 1/1581 to 1/304 cells (p=0.009), as shown in Table 7, herein below.

TABLE 7

| Passage | No of cells injected | Engraftment rate | Stem cell frequency |
|---|---|---|---|
| early | 1000 | 3/4 | 1/1581 |
| | 500 | 3/4 | |
| | 100 | 0/4 | |
| Late | 1000 | 3/4 | 1/304 |
| | 500 | 4/4 | |
| | 100 | 2/4 | |
| | 50 | 1/4 | |
| | 10 | 0/4 | |

A Gene heat map is provided in FIG. 9, comparing the expression pattern of several proliferation markers (e.g. K167, E2F2, and CDK1), self renewal polycomb genes (e.g. BMI1, TOP2A, and EZH2), and metastasis signature genes (e.g. SPARC, CXCR4 and LTBP1), between the different PPB samples, adult lung (AL) and fetal lung (FL) revealed that high passages are highly proliferative and presenting up-regulation of self renewal genes, with an invasive gene signature, predicting metastatic behavior.

Immunohistochemistry (IHC) of several Xn passage (P4, P8, P12 and P17) for NCAM1 reveals increased expression with Xn serial propagation as illustrated in FIG. 10A. qRT-PCR analysis revealed high NCAM1 expression in the primary tumor in comparison to adult lung control (right) and high NCAM1 expression in fetal lung in comparison to adult lung (left) emphasizing the fact that NCAM1 plays an important role during carcinogenesis and development (FIG. 10B).

IHC of several Xn passage (P4, P8, P12 and P17) for CD44 reveals increased expression with Xn serial propagation, as illustrated in FIGS. 11A-B.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of identifying cancer stem cell markers in a human primary tumor selected from the group consisting of breast cancer, medulloblastoma, atypical teratoid/rhabdoid tumor (ATRT), Ewing's sarcoma, Pleuropulmonary Blastoma and Wilms' tumor, the method comprising:
   (a) in vivo passaging serial dilutions of the primary tumor for at least 10 passages to increase a tumor aggressiveness phenotype of the primary tumor, wherein cells of the primary tumor and passaged cells of the primary tumor are not subjected to immunoisolation and wherein said tumor aggressiveness phenotype is selected from the group consisting of time to tumor formation and amount of cells for tumor formation; and
   (b) isolating cells of the tumor following step (a) to generate a first population of passaged tumor cells; and
   (c) measuring a level of at least one antigen in said first population of passaged tumor cells of the primary tumor and measuring a level of said at least one antigen in a second population of tumor cells of the primary tumor, and wherein said second population of tumor cells are of are of a serial dilution of said first population of passaged tumor cells:
      (i) non-passaged cells of the human primary tumor; or
      (ii) in vivo passaged cells of the human primary tumor, wherein said second population of tumor cells has been in vivo passaged for at least one less number of passages than said first population of passaged tumor cell,
   wherein an increase in the amount of said antigen in said first population of tumor cells as compared to the amount of said antigen in said second population of tumor cells is indicative of a cancer stem cell marker in the human primary tumor.

2. The method of claim 1, wherein said antigen is a polypeptide.

3. The method of claim 1, wherein said second population of tumor cells are sequentially passaged in vivo for no more than 5 passages.

4. The method of claim 1, wherein said passaging is effected in mice.

5. The method of claim 1, wherein said passaging is effected by implanting into an animal non-dissociated cells of a tissue sample of a xenograft of the primary tumor.

6. The method of claim 1, wherein said passaging is effected by implanting into an animal a single cell suspension of a xenograft of the primary tumor.

7. The method of claim 1, wherein said first population of passaged cells are passaged in vivo for 10-30 passages.

8. The method of claim 1, wherein said first population of passaged cells are passaged in vivo for 10-20 passages.

9. The method of claim 1, comprising isolating a cancer stem cell using the identified cancer stem cell marker.

\* \* \* \* \*